US011603392B2

(12) United States Patent
Yang et al.

(10) Patent No.: US 11,603,392 B2
(45) Date of Patent: Mar. 14, 2023

(54) VAULT PARTICLES HAVING A MODIFIED R8 FLEXIBLE REGION

(71) Applicant: The Regents of the University of California, Oakland, CA (US)

(72) Inventors: Otto O. Yang, Los Angeles, CA (US); Ke Ding, Los Angeles, CA (US); Jan Mrazek, Los Angeles, CA (US); Z. Hong Zhou, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 104 days.

(21) Appl. No.: 16/759,325

(22) PCT Filed: Oct. 30, 2018

(86) PCT No.: PCT/US2018/058127
§ 371 (c)(1),
(2) Date: Apr. 25, 2020

(87) PCT Pub. No.: WO2019/089529
PCT Pub. Date: May 9, 2019

(65) Prior Publication Data
US 2020/0255488 A1  Aug. 13, 2020

Related U.S. Application Data

(60) Provisional application No. 62/579,303, filed on Oct. 31, 2017.

(51) Int. Cl.
*C07K 14/47* (2006.01)
*A61K 39/39* (2006.01)
*A61K 38/00* (2006.01)

(52) U.S. Cl.
CPC ............. *C07K 14/47* (2013.01); *A61K 39/39* (2013.01); *A61K 38/00* (2013.01)

(58) Field of Classification Search
None
See application file for complete search history.

(56) References Cited

FOREIGN PATENT DOCUMENTS

| WO | 2016049122 | 3/2016 | | |
|---|---|---|---|---|
| WO | WO-2016049122 A1 * | 3/2016 | ............. | A61K 38/38 |

OTHER PUBLICATIONS

Benner et al. "Vault Nanoparticles: Chemical Modifications for Imaging and Enhanced Delivery" ACS Nano 11:872-881. (Year: 2017).*
Tang et al. "14-3-3epsilon Boosts Bleomycin-induced DNA Damage Response by Inhibiting the Drug-Resistant Activity of MVP" J. Proteome Res. 12:2511-2524. (Year: 2013).*
Tanaka et al. "The Structure of Rat Liver Vaultat 3.5 Angstrom Resolution" Science 323:384-388. (Year: 2009).*
Kar et al. "Novel CCL21-Vault Nanocapsule Intratumoral Delivery Inhibits Lung Cancer Growth" PLoS ONE 6:e18758. (Year: 2011).*
NCBI Reference Sequence: XP_009007665.2 (Year: 2020).*
NCBI Reference Sequence: XP_028630948.1 (Year: 2019).*
NCBI Reference Sequence: XP_031244220.1 (Year: 2019).*
NCBI Reference Sequence: XP_030653962.1 (Year: 2019).*
NCBI Reference Sequence: XP_032099054.1 (Year: 2020).*
NCBI Reference Sequence: XP_012319937.2 (Year: 2017).*
NCBI Reference Sequence: XP_005064435.1 (Year: 2021).*
GenBank: ERE80180.1 (Year: 2015).*
Bhaskar & Lim, "Engineering protein nanocages as carriers for biomedical applications", Apr. 7, 2017, p. e371, vol. 9, No. 4, Publisher NPG Asia Mater.
Extended European Search Report received in EP 18874076.5, dated Jul. 19, 2021.
International Search Report received in PCT/US2018/058127, dated Jan. 22, 2019.
Written Opinion received in PCT/US2018/058127, dated Jan. 22, 2019.
Benner et al., "Vault Nanoparticles: Chemical Modifications for Imaging and Enhanced Delivery", Jan. 24, 2017, pp. 872-881, vol. 11, No. 1, Publisher: ACS Nano.
Tang et al., "14-3-3E Boosts Bleomycin-induced DNA Damage Response by Inhibiting the Drug-Resistant Activity of MVP", Jun. 7, 2013, pp. 2511-2524, vol. 12, No. 6, Publisher: J Proteome Res 12(6): 25112524.

* cited by examiner

*Primary Examiner* — Sudhakar Katakam
*Assistant Examiner* — Zachary J Miknis
(74) *Attorney, Agent, or Firm* — Suzannah K. Sundby, Esq.; Canady + Lortz LLP

(57) ABSTRACT

Disclosed herein are major vault proteins having modified R8 flexible regions, vault particles comprising major vault proteins having modified R8 flexible regions, and methods of packaging passenger polypeptides in the modified R8 flexible regions.

24 Claims, 14 Drawing Sheets

Specification includes a Sequence Listing.

SEQUENCE LISTING

<160> NUMBER OF SEQ ID NOS: 31

<210> SEQ ID NO 1
<211> LENGTH: 66
<212> TYPE: DNA
<213> ORGANISM: Artificial Sequence
<220> FEATURE:
<223> OTHER INFORMATION: R8 flexible region of human major vault protein
      (MVP)

<400> SEQUENCE: 1
aacaaggggc aggaccctct ggcagacagg ggtgagaagg acacagctaa gagcctccag    60
cccttg                                                              66

<210> SEQ ID NO 2
<211> LENGTH: 72
<212> TYPE: DNA
<213> ORGANISM: Artificial Sequence
<220> FEATURE:
<223> OTHER INFORMATION: Modified R8 flexible region having an AfeI
      restriction enzyme site inserted therein

<400> SEQUENCE: 2
aacaaggggc aggaccctct ggcagacagg ggtagcgctg agaaggacac agctaagagc    60 ctccagcccct tg                                                      72

<210> SEQ ID NO 3
<211> LENGTH: 22
<212> TYPE: PRT
<213> ORGANISM: Artificial Sequence
<220> FEATURE:
<223> OTHER INFORMATION: Human MVP from amino acids 428-449

<400> SEQUENCE: 3

Asn Lys Gly Gln Asp Pro Leu Ala Asp Arg Gly Glu Lys Asp Thr Ala
1               5                   10                  15

Lys Ser Leu Gln Pro Leu
            20

<210> SEQ ID NO 4
<211> LENGTH: 32
<212> TYPE: PRT
<213> ORGANISM: Artificial Sequence
<220> FEATURE:
<223> OTHER INFORMATION: Example of R8 flexible loop sequence

<400> SEQUENCE: 4

Val Glu Glu Leu Leu Asn Lys Gly Gln Asp Pro Leu Ala Asp Arg Gly
1               5                   10                  15

Glu Lys Asp Thr Ala Lys Ser Leu Gln Pro Leu Ala Pro Arg Asn Lys
            20                  25                  30

<210> SEQ ID NO 5
<211> LENGTH: 15
<212> TYPE: PRT
<213> ORGANISM: Artificial Sequence
<220> FEATURE:
<223> OTHER INFORMATION: Example of flexible amino acid linker

<400> SEQUENCE: 5

Gly Gly Gly Gly Ser Gly Gly Gly Ser Gly Gly Gly Gly Ser
1               5                   10                  15

<210> SEQ ID NO 6

```
<211> LENGTH: 5
<212> TYPE: PRT
<213> ORGANISM: Artificial Sequence
<220> FEATURE:
<223> OTHER INFORMATION: Example of flexible amino acid linker

<400> SEQUENCE: 6

Gly Phe Leu Gly Leu
1               5

<210> SEQ ID NO 7
<211> LENGTH: 893
<212> TYPE: PRT
<213> ORGANISM: Artificial Sequence
<220> FEATURE:
<223> OTHER INFORMATION: Human Major Vault Protein (MVP)

<400> SEQUENCE: 7

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
    50                  55                  60

Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
    130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255

Glu Ala His Val Pro Asp Val His Glu Glu Val Leu Gly Val Val Pro
            260                 265                 270

Ile Thr Thr Leu Gly Pro His Asn Tyr Cys Val Ile Leu Asp Pro Val
        275                 280                 285

Gly Pro Asp Gly Lys Asn Gln Leu Gly Gln Lys Arg Val Val Lys Gly
    290                 295                 300
```

```
Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
            325                 330                 335

Leu Gln Pro Leu Glu Glu Gly Glu Asp Glu Lys Val Ser His Gln
        340                 345                 350

Ala Gly Asp His Trp Leu Ile Arg Gly Pro Leu Glu Tyr Val Pro Ser
            355                 360                 365

Ala Lys Val Glu Val Val Glu Glu Arg Gln Ala Ile Pro Leu Asp Glu
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Pro Gly Val Glu Glu Leu Leu Asn Lys Gly Gln Asp
            420                 425                 430

Pro Leu Ala Asp Arg Gly Glu Lys Asp Thr Ala Lys Ser Leu Gln Pro
        435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605

Ser Glu Ala Lys Gly Pro Asp Gly Met Ala Leu Pro Arg Pro Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Leu Glu Leu Glu Ala Leu Ser Met Ala Val Glu Ser Thr Gly
705                 710                 715                 720
```

-continued

```
Thr Ala Lys Ala Glu Ala Glu Ser Arg Ala Glu Ala Arg Ile Glu
            725                 730                 735

Gly Glu Gly Ser Val Leu Gln Ala Lys Leu Lys Ala Gln Ala Leu Ala
        740                 745                 750

Ile Glu Thr Glu Ala Glu Leu Gln Arg Val Gln Lys Val Arg Glu Leu
            755                 760                 765

Glu Leu Val Tyr Ala Arg Ala Gln Leu Glu Leu Glu Val Ser Lys Ala
        770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
            805                 810                 815

Met Gln Val Lys Leu Leu Gln Ser Leu Gly Leu Lys Ser Thr Leu Ile
        820                 825                 830

Thr Asp Gly Ser Thr Pro Ile Asn Leu Phe Asn Thr Ala Phe Gly Leu
    835                 840                 845

Leu Gly Met Gly Pro Glu Gly Gln Pro Leu Gly Arg Arg Val Ala Ser
    850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
            885                 890

<210> SEQ ID NO 8
<211> LENGTH: 26
<212> TYPE: DNA
<213> ORGANISM: Artificial Sequence
<220> FEATURE:
<223> OTHER INFORMATION: Human Major Vault Protein (MVP) forward primer

<400> SEQUENCE: 8
gctgagaagg acacagctaa gagcct                                       26

<210> SEQ ID NO 9
<211> LENGTH: 26
<212> TYPE: DNA
<213> ORGANISM: Artificial Sequence
<220> FEATURE:
<223> OTHER INFORMATION: Human Major Vault Protein (MVP) reverse primer

<400> SEQUENCE: 9
gctacccctg tctgccagag ggtcct                                       26

<210> SEQ ID NO 10
<211> LENGTH: 204
<212> TYPE: DNA
<213> ORGANISM: Artificial Sequence
<220> FEATURE:
<223> OTHER INFORMATION: HIV Gag1-M1 insert
<220> FEATURE:
<221> NAME/KEY: CDS
<222> LOCATION: (1)..(204)

<400> SEQUENCE: 10 atg acc ccc cgg acc ctg aac gcc tgg gtc aag gtg gtg gaa gag aag    48
Met Thr Pro Arg Thr Leu Asn Ala Trp Val Lys Val Val Glu Glu Lys
1               5                   10                  15 gcc ttc agc ccc gaa gtg atc ccc atg ttc acc gcc ctg agc gag ggc    96
Ala Phe Ser Pro Glu Val Ile Pro Met Phe Thr Ala Leu Ser Glu Gly
            20                  25                  30
```

-continued

```
gcc acc ccc agc gac ctg aac acc atg ctg aat acc atc ggc ggc cac      144
Ala Thr Pro Ser Asp Leu Asn Thr Met Leu Asn Thr Ile Gly Gly His
         35                  40                  45 cag gcc gcc atg cag atg ctg aag gac acc atc aac gaa gag gcc gcc      192
Gln Ala Ala Met Gln Met Leu Lys Asp Thr Ile Asn Glu Glu Ala Ala
 50                  55                  60 gag tgg gac cgg                                                       204
Glu Trp Asp Arg
 65

<210> SEQ ID NO 11
<211> LENGTH: 68
<212> TYPE: PRT
<213> ORGANISM: Artificial Sequence
<220> FEATURE:
<223> OTHER INFORMATION: Synthetic Construct

<400> SEQUENCE: 11

Met Thr Pro Arg Thr Leu Asn Ala Trp Val Lys Val Val Glu Glu Lys
  1               5                  10                  15

Ala Phe Ser Pro Glu Val Ile Pro Met Phe Thr Ala Leu Ser Glu Gly
             20                  25                  30

Ala Thr Pro Ser Asp Leu Asn Thr Met Leu Asn Thr Ile Gly Gly His
         35                  40                  45

Gln Ala Ala Met Gln Met Leu Lys Asp Thr Ile Asn Glu Glu Ala Ala
 50                  55                  60

Glu Trp Asp Arg
 65

<210> SEQ ID NO 12
<211> LENGTH: 261
<212> TYPE: DNA
<213> ORGANISM: Artificial Sequence
<220> FEATURE:
<223> OTHER INFORMATION: HIV Gag2-M1 insert
<220> FEATURE:
<221> NAME/KEY: CDS
<222> LOCATION: (1)..(261)

<400> SEQUENCE: 12 atg aac ccc ccc atc ccc gtg ggc gac atc tac aag cgg tgg atc atc      48
Met Asn Pro Pro Ile Pro Val Gly Asp Ile Tyr Lys Arg Trp Ile Ile
  1               5                  10                  15 ctg ggc ctg gac aag atc gtg cgg atg tac agc ccc acc agc atc ctg      96
Leu Gly Leu Asp Lys Ile Val Arg Met Tyr Ser Pro Thr Ser Ile Leu
             20                  25                  30 gac atc cgg cag ggc ccc aaa gag ccc ttc cgg gac tac gtg gac cgg      144
Asp Ile Arg Gln Gly Pro Lys Glu Pro Phe Arg Asp Tyr Val Asp Arg
         35                  40                  45 ttc ttc aag gtg ctg cgg gcc gag cag gcc acc cag gac gtg aag aac      192
Phe Phe Lys Val Leu Arg Ala Glu Gln Ala Thr Gln Asp Val Lys Asn
 50                  55                  60 tgg atg acc gac acc ctg ctg gtg cag aac gcc aac ccc gac tgc aag      240
Trp Met Thr Asp Thr Leu Leu Val Gln Asn Ala Asn Pro Asp Cys Lys
 65                  70                  75                  80 acc atc ctg aga gcc ctg ggc                                          261
Thr Ile Leu Arg Ala Leu Gly
                 85

<210> SEQ ID NO 13
<211> LENGTH: 87
<212> TYPE: PRT
```

<210> ORGANISM: Artificial Sequence
<220> FEATURE:
<223> OTHER INFORMATION: Synthetic Construct

<400> SEQUENCE: 13

```
Met Asn Pro Pro Ile Pro Val Gly Asp Ile Tyr Lys Arg Trp Ile Ile
1               5                   10                  15

Leu Gly Leu Asp Lys Ile Val Arg Met Tyr Ser Pro Thr Ser Ile Leu
            20                  25                  30

Asp Ile Arg Gln Gly Pro Lys Glu Pro Phe Arg Asp Tyr Val Asp Arg
        35                  40                  45

Phe Phe Lys Val Leu Arg Ala Glu Gln Ala Thr Gln Asp Val Lys Asn
    50                  55                  60

Trp Met Thr Asp Thr Leu Leu Val Gln Asn Ala Asn Pro Asp Cys Lys
65                  70                  75                  80

Thr Ile Leu Arg Ala Leu Gly
                85
```

<210> SEQ ID NO 14
<211> LENGTH: 261
<212> TYPE: DNA
<213> ORGANISM: Artificial Sequence
<220> FEATURE:
<223> OTHER INFORMATION: HIV Env-M1 insert
<220> FEATURE:
<221> NAME/KEY: CDS
<222> LOCATION: (1)..(261)

<400> SEQUENCE: 14

```
atg ggc ttt ctg ggc gtg gcc ggc agc aca atg gga gcc gcc agc atc      48
Met Gly Phe Leu Gly Val Ala Gly Ser Thr Met Gly Ala Ala Ser Ile
1               5                   10                  15 acc ctg acc gtg cag gcc aga cag ctg ctg agc ggc atc gtg cag cag      96
Thr Leu Thr Val Gln Ala Arg Gln Leu Leu Ser Gly Ile Val Gln Gln
            20                  25                  30 cag agc aac ctg ctg aga gct atc gag gcc cag cag cat ctg ctg aag     144
Gln Ser Asn Leu Leu Arg Ala Ile Glu Ala Gln Gln His Leu Leu Lys
        35                  40                  45 ctg acc gtg tgg ggc atc aag cag ctg cag acc cgg gtg ctg gcc atc     192
Leu Thr Val Trp Gly Ile Lys Gln Leu Gln Thr Arg Val Leu Ala Ile
    50                  55                  60 gag aga tac ctg aag gac cag cag ctc ctg ggc ctg tgg ggc tgc agc     240
Glu Arg Tyr Leu Lys Asp Gln Gln Leu Leu Gly Leu Trp Gly Cys Ser
65                  70                  75                  80 ggc aag ctg atc tgc ccc acc                                         261
Gly Lys Leu Ile Cys Pro Thr
                85
```

<210> SEQ ID NO 15
<211> LENGTH: 87
<212> TYPE: PRT
<213> ORGANISM: Artificial Sequence
<220> FEATURE:
<223> OTHER INFORMATION: Synthetic Construct

<400> SEQUENCE: 15

```
Met Gly Phe Leu Gly Val Ala Gly Ser Thr Met Gly Ala Ala Ser Ile
1               5                   10                  15

Thr Leu Thr Val Gln Ala Arg Gln Leu Leu Ser Gly Ile Val Gln Gln
            20                  25                  30

Gln Ser Asn Leu Leu Arg Ala Ile Glu Ala Gln Gln His Leu Leu Lys
        35                  40                  45
```

```
Leu Thr Val Trp Gly Ile Lys Gln Leu Gln Thr Arg Val Leu Ala Ile
 50                  55                  60

Glu Arg Tyr Leu Lys Asp Gln Gln Leu Leu Gly Leu Trp Gly Cys Ser
 65                  70                  75                  80

Gly Lys Leu Ile Cys Pro Thr
                85

<210> SEQ ID NO 16
<211> LENGTH: 132
<212> TYPE: DNA
<213> ORGANISM: Artificial Sequence
<220> FEATURE:
<223> OTHER INFORMATION: HIV Nef-M1 insert
<220> FEATURE:
<221> NAME/KEY: CDS
<222> LOCATION: (1)..(132)

<400> SEQUENCE: 16 atg cgg cag gaa atc ctg gac ctc tgg gtg tac cac acc cag gga ttc      48
Met Arg Gln Glu Ile Leu Asp Leu Trp Val Tyr His Thr Gln Gly Phe
 1               5                  10                  15 ttc cca gac tgg cag aac tac acc ccc gga ccc ggc atc aga tac ccc      96
Phe Pro Asp Trp Gln Asn Tyr Thr Pro Gly Pro Gly Ile Arg Tyr Pro
             20                  25                  30 ctg acc ttc ggc tgg tgc tac aag ctg gtg ccc gtg                     132
Leu Thr Phe Gly Trp Cys Tyr Lys Leu Val Pro Val
         35                  40

<210> SEQ ID NO 17
<211> LENGTH: 44
<212> TYPE: PRT
<213> ORGANISM: Artificial Sequence
<220> FEATURE:
<223> OTHER INFORMATION: Synthetic Construct

<400> SEQUENCE: 17

Met Arg Gln Glu Ile Leu Asp Leu Trp Val Tyr His Thr Gln Gly Phe
 1               5                  10                  15

Phe Pro Asp Trp Gln Asn Tyr Thr Pro Gly Pro Gly Ile Arg Tyr Pro
             20                  25                  30

Leu Thr Phe Gly Trp Cys Tyr Lys Leu Val Pro Val
         35                  40

<210> SEQ ID NO 18
<211> LENGTH: 38
<212> TYPE: DNA
<213> ORGANISM: Artificial Sequence
<220> FEATURE:
<223> OTHER INFORMATION: HIV Gag1-M1 forward primer

<400> SEQUENCE: 18
ggcagacagg ggtagcatga ccccccggac cctgaacg                            38

<210> SEQ ID NO 19
<211> LENGTH: 37
<212> TYPE: DNA
<213> ORGANISM: Artificial Sequence
<220> FEATURE:
<223> OTHER INFORMATION: HIV Gag1-M1 reverse primer

<400> SEQUENCE: 19
gctgtgtcct tctcagcccg gtcccactcg gcggcct                             37
```

```
<210> SEQ ID NO 20
<211> LENGTH: 36
<212> TYPE: DNA
<213> ORGANISM: Artificial Sequence
<220> FEATURE:
<223> OTHER INFORMATION: HIV Gag2-M1 forward primer

<400> SEQUENCE: 20
ggcagacagg ggtagcatga accccccat ccccgt                              36

<210> SEQ ID NO 21
<211> LENGTH: 37
<212> TYPE: DNA
<213> ORGANISM: Artificial Sequence
<220> FEATURE:
<223> OTHER INFORMATION: HIV Gag2-M1 reverse primer

<400> SEQUENCE: 21
gctgtgtcct tctcagcgcc cagggctctc aggatgg                            37

<210> SEQ ID NO 22
<211> LENGTH: 36
<212> TYPE: DNA
<213> ORGANISM: Artificial Sequence
<220> FEATURE:
<223> OTHER INFORMATION: HIV Env-M1 forward primer

<400> SEQUENCE: 22
ggcagacagg ggtagcatgg gctttctggg cgtggc                             36

<210> SEQ ID NO 23
<211> LENGTH: 36
<212> TYPE: DNA
<213> ORGANISM: Artificial Sequence
<220> FEATURE:
<223> OTHER INFORMATION: HIV Env-M1 reverse primer

<400> SEQUENCE: 23
gctgtgtcct tctcagcggt ggggcagatc agcttg                             36

<210> SEQ ID NO 24
<211> LENGTH: 36
<212> TYPE: DNA
<213> ORGANISM: Artificial Sequence
<220> FEATURE:
<223> OTHER INFORMATION: HIV Nef-M1 forward primer

<400> SEQUENCE: 24
ggcagacagg ggtagcatgc ggcaggaaat cctgga                             36

<210> SEQ ID NO 25
<211> LENGTH: 36
<212> TYPE: DNA
<213> ORGANISM: Artificial Sequence
<220> FEATURE:
<223> OTHER INFORMATION: HIV Nef-M1 reverse primer

<400> SEQUENCE: 25
gctgtgtcct tctcagccac gggcaccagc ttgtag                             36

<210> SEQ ID NO 26
<211> LENGTH: 708
<212> TYPE: DNA
<213> ORGANISM: Artificial Sequence
<220> FEATURE:
<223> OTHER INFORMATION: mCherry insert
<220> FEATURE:
```

<221> NAME/KEY: CDS
<222> LOCATION: (1)..(708)

<400> SEQUENCE: 26

```
atg gtg agc aag ggc gag gag gat aac atg gcc atc atc aag gag ttc      48
Met Val Ser Lys Gly Glu Glu Asp Asn Met Ala Ile Ile Lys Glu Phe
1               5                   10                  15 atg cgc ttc aag gtg cac atg gag ggc tcc gtg aac ggc cac gag ttc      96
Met Arg Phe Lys Val His Met Glu Gly Ser Val Asn Gly His Glu Phe
                20                  25                  30 gag atc gag ggc gag ggc gag ggc cgc ccc tac gag ggc acc cag acc     144
Glu Ile Glu Gly Glu Gly Glu Gly Arg Pro Tyr Glu Gly Thr Gln Thr
            35                  40                  45 gcc aag ctg aag gtg acc aag ggt ggc ccc ctg ccc ttc gcc tgg gac     192
Ala Lys Leu Lys Val Thr Lys Gly Gly Pro Leu Pro Phe Ala Trp Asp
        50                  55                  60 atc ctg tcc cct cag ttc atg tac ggc tcc aag gcc tac gtg aag cac     240
Ile Leu Ser Pro Gln Phe Met Tyr Gly Ser Lys Ala Tyr Val Lys His
65                  70                  75                  80 ccc gcc gac atc ccc gac tac ttg aag ctg tcc ttc ccc gag ggc ttc     288
Pro Ala Asp Ile Pro Asp Tyr Leu Lys Leu Ser Phe Pro Glu Gly Phe
                85                  90                  95 aag tgg gag cgc gtg atg aac ttc gag gac ggc ggc gtg gtg acc gtg     336
Lys Trp Glu Arg Val Met Asn Phe Glu Asp Gly Gly Val Val Thr Val
                100                 105                 110 acc cag gac tcc tcc ctg cag gac ggc gag ttc atc tac aag gtg aag     384
Thr Gln Asp Ser Ser Leu Gln Asp Gly Glu Phe Ile Tyr Lys Val Lys
            115                 120                 125 ctg cgc ggc acc aac ttc ccc tcc gac ggc ccc gta atg cag aag aag     432
Leu Arg Gly Thr Asn Phe Pro Ser Asp Gly Pro Val Met Gln Lys Lys
        130                 135                 140 acc atg ggc tgg gag gcc tcc tcc gag cgg atg tac ccc gag gac ggc     480
Thr Met Gly Trp Glu Ala Ser Ser Glu Arg Met Tyr Pro Glu Asp Gly
145                 150                 155                 160 gcc ctg aag ggc gag atc aag cag agg ctg aag ctg aag gac ggc ggc     528
Ala Leu Lys Gly Glu Ile Lys Gln Arg Leu Lys Leu Lys Asp Gly Gly
                165                 170                 175 cac tac gac gct gag gtc aag acc acc tac aag gcc aag aag ccc gtg     576
His Tyr Asp Ala Glu Val Lys Thr Thr Tyr Lys Ala Lys Lys Pro Val
                180                 185                 190 cag ctg ccc ggc gcc tac aac gtc aac atc aag ttg gac atc acc tcc     624
Gln Leu Pro Gly Ala Tyr Asn Val Asn Ile Lys Leu Asp Ile Thr Ser
            195                 200                 205 cac aac gag gac tac acc atc gtg gaa cag tac gaa cgc gcc gag ggc     672
His Asn Glu Asp Tyr Thr Ile Val Glu Gln Tyr Glu Arg Ala Glu Gly
        210                 215                 220 cgc cac tcc acc ggc ggc atg gac gag ctg tac aag                     708
Arg His Ser Thr Gly Gly Met Asp Glu Leu Tyr Lys
225                 230                 235
```

<210> SEQ ID NO 27
<211> LENGTH: 236
<212> TYPE: PRT
<213> ORGANISM: Artificial Sequence
<220> FEATURE:
<223> OTHER INFORMATION: Synthetic Construct

<400> SEQUENCE: 27

```
Met Val Ser Lys Gly Glu Glu Asp Asn Met Ala Ile Ile Lys Glu Phe
1               5                   10                  15
```

```
Met Arg Phe Lys Val His Met Glu Gly Ser Val Asn Gly His Glu Phe
             20                  25                  30
Glu Ile Glu Gly Glu Gly Glu Gly Arg Pro Tyr Glu Gly Thr Gln Thr
         35                  40                  45
Ala Lys Leu Lys Val Thr Lys Gly Gly Pro Leu Pro Phe Ala Trp Asp
 50                  55                  60
Ile Leu Ser Pro Gln Phe Met Tyr Gly Ser Lys Ala Tyr Val Lys His
 65                  70                  75                  80
Pro Ala Asp Ile Pro Asp Tyr Leu Lys Leu Ser Phe Pro Glu Gly Phe
                 85                  90                  95
Lys Trp Glu Arg Val Met Asn Phe Glu Asp Gly Gly Val Val Thr Val
            100                 105                 110
Thr Gln Asp Ser Ser Leu Gln Asp Gly Glu Phe Ile Tyr Lys Val Lys
        115                 120                 125
Leu Arg Gly Thr Asn Phe Pro Ser Asp Gly Pro Val Met Gln Lys Lys
130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
        195                 200                 205
His Asn Glu Asp Tyr Thr Ile Val Glu Gln Tyr Glu Arg Ala Glu Gly
    210                 215                 220
Arg His Ser Thr Gly Gly Met Asp Glu Leu Tyr Lys
225                 230                 235
```

```
<210> SEQ ID NO 28
<211> LENGTH: 40
<212> TYPE: DNA
<213> ORGANISM: Artificial Sequence
<220> FEATURE:
<223> OTHER INFORMATION: mCherry forward primer

<400> SEQUENCE: 28
ggcagacagg ggtagcatgg tgagcaaggg cgaggaggat                        40

<210> SEQ ID NO 29
<211> LENGTH: 36
<212> TYPE: DNA
<213> ORGANISM: Artificial Sequence
<220> FEATURE:
<223> OTHER INFORMATION: mCherry reverse primer

<400> SEQUENCE: 29
gctgtgtcct tctcagcctt gtacagctcg tccatg                            36

<210> SEQ ID NO 30
<211> LENGTH: 27
<212> TYPE: DNA
<213> ORGANISM: Artificial Sequence
<220> FEATURE:
<223> OTHER INFORMATION: AfeI site forward primer

<400> SEQUENCE: 30
gctttggcgc cccggaacaa gacccgt                                      27
```

```
<210> SEQ ID NO 31
<211> LENGTH: 28
<212> TYPE: DNA
<213> ORGANISM: Artificial Sequence
<220> FEATURE:
<223> OTHER INFORMATION: AfeI site reverse primer

<400> SEQUENCE: 31
gctgttcagc agctcctcca ccccggga                                          28
```

VAULT PARTICLES HAVING A MODIFIED R8 FLEXIBLE REGION

CROSS REFERENCE TO RELATED APPLICATION DATA

This application claims the benefit of U.S. Application No. 62/579,303, filed Oct. 31, 2017, which is herein incorporated by reference in its entirety.

ACKNOWLEDGEMENT OF GOVERNMENT SUPPORT

This invention was made with Government support under Grant Number GM071940, awarded by the National Institutes of Health. The Government has certain rights in the invention.

REFERENCE TO A SEQUENCE LISTING SUBMITTED VIA EFS-WEB

The content of the ASCII text file of the sequence listing named "20171031_034044_176P1_seq_ST25" which is 25.7 kb in size was created on Oct. 31, 2017, and electronically submitted via EFS-Web herewith the application is incorporated herein by reference in its entirety.

BACKGROUND OF THE INVENTION

1. Field of the Invention

The present invention relates to recombinant vault particles having a modified region in the R8 domain of its major vault protein (MVP).

2. Description of the Related Art

Vaults are cytoplasmic ubiquitous ribonucleoprotein particles first described in 1986 that are found in most eukaryotic cells. See Kedersha & Rome (1986) J Cell Biol 103 (3):699-709. Native vaults are about 12.9±1 MDa ovoid spheres with overall dimensions of about 72 nm×42 nm×42 nm. Each native vault has a mass of 13 MDa and is composed of multiple copies of at least three different proteins—the major vault protein (MVP, 100 kDa), vault poly(ADP-ribose) polymerase (VPARP), and telomerase-associated protein 1 (TEP1)—and several copies of small untranslated vault-associated RNA (vRNAs).

Early structural characterization of vaults was accomplished by cryo electron microscopy (cryoEM) and single particle analysis with resolution limited to about 31 Å, mainly due to the low image contrast and the featureless nature of the vault (Kong et al., 1999). D48 symmetry was applied to this early cryoEM structure (Kong et al., 1999) and the first X-ray crystal structure at 9 Å resolution (Anderson et al., 2007). Subsequently, another crystal structure of the rat native vault has been solved with D39 symmetry at 3.5 Å resolution (PDB 4V60) (Tanaka et al., 2009). Of the 861-amino-acid (aa) long MVP, PDB 4V60 contains full atom models for amino acid residues (aa). 1-427, 449-607,621-813, and Cα-only model for the C-terminal segment (aa 814-845), with a prominent gap from aa 428-448 have been solved. From the N- to C-terminus, each MVP monomer consists of a body region containing 9 repeats (domains R1-R9) of an antiparallel β-sheet fold, followed by a shoulder region containing a single domain with 4 α-helices and a 4-stranded β-sheet, and a cap region containing a 155-amino-acid-long cap-helix domain and a cap-ring domain. In this crystal structure, the Cα-only model for the C-terminal segment is encapsulated inside the vault, rather than being exposed outside the vault (Kickhoefer et al., 2009). A crystal structure of a truncated MVP monomer (PDB 3GF5, which contains only the first, N-terminal 387 aa residues) has also been solved to 2.1 Å resolution (Querol-Audi et al., 2009). These two crystal structures (PDB 4V60 for the vault and PDB 3GF5 for the N terminal segment) differ in the main chain tracing near the N-terminus (R1 and R2 domain). Further model refinement based on the electron density map of PDB 4V60 yielded a new model (PDB 4HL8) (Casanas et al., 2013). This refined, new model is basically a montage of PDB 3GF5 and 4V60: with its N-terminal domains (R1 and R2) similar to PDB 3GF5 and the following domains similar to those in PDB 4V60. Because PDB 3DF5 was obtained from a crystal containing segmented MVP, which lacked constraints from neighboring MVP monomers as those in the assembled vault, N-terminus domains in PDB 3GF5 are less curved than those in PDB 4HL8.

Recombinant vaults have been produced using a baculovirus expression system and passenger molecules have been encapsulated therein as, e.g., heterologous proteins recombinantly fused to the major vault protein interaction domain (mINT) of VPARP (Stephen, et al. (2001). Passenger molecules may also be packaged with a vault by recombinantly fusing the passenger molecules to the N-terminus or C-terminus of one or more MVP monomers forming the vault. Passenger molecules recombinantly fused to the N-terminus of MVP are located inside the vault at the waist of the barrel (Mikyas et al., 2004), while those fused to the C-terminus are located outside the vault at its two poles of the barrel (Kickhoefer et al., 2009). Recombinant vaults have also been made using cell-free techniques and, in addition to packaging by recombinant fusion techniques, molecules present in the synthesis mixtures may be passively packaged within the vault structure during its formation. See WO 2016/049122.

Unfortunately, mINT fusion packaging is both unpredictable and inconsistent as successful packaging depends on the given passenger molecule and can vary from batch to batch; certain passenger molecules covalently attached to the N-terminus of an MVP protein can disrupt and/or prevent the formation of the vault structure; and passive packaging is limited to certain types and concentrations of molecules, which can also escape from the vault before the vault is delivered to its target site.

SUMMARY OF THE INVENTION

In some embodiments, the present invention provides a modified MVP R8 protein that comprises an MVP protein having one or more amino acid substitutions, additions, and/or deletions in its R8 flexible region. In some embodiments, the MVP protein is as described herein (see, e.g., [0043]) and the R8 flexible region is as described herein (see, e.g., [0056]) or is a modified R8 flexible region as described herein (see, e.g., [0057]). In some embodiments, the MVP protein has about 90-100%, more preferably about 95-100%, and most preferably 97-100% sequence identity to human MVP and the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4. In some embodiments, the MVP protein has about 90-100%, more preferably about 95-100%, and most preferably 97-100% sequence identity to human MVP and the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4 and the modified MVP R8 protein is capable of forming a recombinant vault. In some embodiments, the MVP protein has about 95-100% sequence identity to human MVP and the R8 flexible region comprises about 15 to 32 amino acid residues of a sequence that has about at least about 85-100%, preferably about 90-100%, sequence identity to SEQ ID NO: 4. In some embodiments, the MVP protein has about 95-100% sequence identity to human MVP and the R8 flexible region comprises about 15 to 32 amino acid residues of a sequence that has about 85-100%, preferably about 90-100%, sequence identity to SEQ ID NO: 4 and the modified MVP R8 protein is capable of forming a recombinant vault. In some embodiments, the nucleic acid molecule encoding the R8 flexible region has a restriction enzyme site inserted therein. In some embodiments, the nucleic acid molecule encoding the R8 flexible region has one or more adapter sequences inserted therein. In some embodiments, the modified MVP R8 protein comprises a passenger molecule is inserted in its R8 flexible region. In some embodiments, up to about 10%, up to about 20%, up to about 30%, up to about 40%, up to about 50%, up to about 60%, up to about 70%, up to about 80%, or up to about 90-95% of the amino acids of the R8 flexible region are substituted, e.g., replaced with a passenger molecule, such as a passenger peptide. In some embodiments, the passenger molecule is covalently attached to the R8 flexible region with a linker. In some embodiments, the passenger molecule can be a passenger peptide. In some embodiments, the passenger peptide has a linker, e.g., a flexible linker, at its N-terminus and/or its C-terminus. In some embodiments, the passenger peptide is a therapeutic protein known in the art, i.e., a protein described in the art as providing a therapeutic benefit to a subject when administered to the subject. In some embodiments, the passenger peptide is an HIV protein or a fragment thereof. In some embodiments, the modified MVP R8 protein comprises an N-linked passenger molecule and/or a C-linked passenger molecule. In some embodiments, the modified MVP R8 protein comprises a passenger molecule and an N-linked passenger molecule and/or a C-linked passenger molecule. In some embodiments, the passenger molecule is the same as the N-linked passenger molecule and/or the C-linked passenger molecule. In some embodiments, the passenger molecule is different from the N-linked passenger molecule and/or the C-linked passenger molecule. In some embodiments, the passenger molecule, the N-linked passenger molecule, and the C-linked passenger molecule are the same. In some embodiments, the passenger molecule, the N-linked passenger molecule, and the C-linked passenger molecule are different.

In some embodiments, the present invention provides a vault particle comprising a modified MVP R8 protein. In some embodiments, the MVP protein is as described herein (see, e.g., [0043]) and the R8 flexible region is as described herein (see, e.g., [0056]) or is a modified R8 flexible region as described herein (see, e.g., [0057]). In some embodiments, the MVP protein has about 90-100%, more preferably about 95-100%, and most preferably 97-100% sequence identity to human MVP and the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4. In some embodiments, the MVP protein has about 90-100%, more preferably about 95-100%, and most preferably 97-100% sequence identity to human MVP and the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4 and the modified MVP R8 protein is capable of forming a recombinant vault. In some embodiments, the MVP protein has about 95-100% sequence identity to human MVP and the R8 flexible region comprises about 15 to 32 amino acid residues of a sequence that has about at least about 85-100%, preferably about 90-100%, sequence identity to SEQ ID NO: 4. In some embodiments, the MVP protein has about 95-100% sequence identity to human MVP and the R8 flexible region comprises about 15 to 32 amino acid residues of a sequence that has about 85-100%, preferably about 90-100%, sequence identity to SEQ ID NO: 4 and the modified MVP R8 protein is capable of forming a recombinant vault. In some embodiments, the nucleic acid molecule encoding the R8 flexible region has a restriction enzyme site inserted therein. In some embodiments, the nucleic acid molecule encoding the R8 flexible region has one or more adapter sequences inserted therein. In some embodiments, the modified MVP R8 protein comprises a passenger molecule is inserted in its R8 flexible region. In some embodiments, up to about 10%, up to about 20%, up to about 30%, up to about 40%, up to about 50%, up to about 60%, up to about 70%, up to about 80%, or up to about 90-95% of the amino acids of the R8 flexible region are substituted, e.g., replaced with a passenger molecule, such as a passenger peptide. In some embodiments, the passenger molecule is covalently attached to the R8 flexible region with a linker. In some embodiments, the passenger molecule can be a passenger peptide. In some embodiments, the passenger peptide is a therapeutic protein known in the art, i.e., a protein described in the art as providing a therapeutic benefit to a subject when administered to the subject. In some embodiments, the passenger peptide is an HIV protein or a fragment thereof. In some embodiments, the modified MVP R8 protein comprises an N-linked passenger molecule and/or a C-linked passenger molecule. In some embodiments, the modified MVP R8 protein comprises a passenger molecule and an N-linked passenger molecule and/or a C-linked passenger molecule. In some embodiments, the passenger molecule is the same as the N-linked passenger molecule and/or the C-linked passenger molecule. In some embodiments, the passenger molecule is different from the N-linked passenger molecule and/or the C-linked passenger molecule. In some embodiments, the passenger molecule, the N-linked passenger molecule, and the C-linked passenger molecule are the same. In some embodiments, the passenger molecule, the N-linked passenger molecule, and the C-linked passenger molecule are different. In some embodiments, the vault particle comprises a passively packaged passenger molecule and/or an mINT passenger molecule. In some embodiments, the passenger molecule is the same as the passenger molecule of the passively packaged passenger molecule and/or the passenger molecule of the mINT passenger molecule. In some embodiments, the passenger molecule is different from the passenger molecule of the passively packaged passenger molecule and/or the passenger molecule of the mINT passenger molecule. In some embodiments, the passively packaged passenger molecule is an adjuvant. In some embodiments, the vault particle has a barrel-like structure.

In some embodiments, the present invention provides a composition comprising one or more modified MVP R8 proteins and/or one or more vault particles as described herein. In some embodiments, the composition comprises an adjuvant and/or a pharmaceutically acceptable carrier.

In some embodiments, the present invention provides a method of administering a passenger molecule to a subject which comprises administering to the subject a modified MVP R8 protein, vault particle, and/or a composition as described herein. In some embodiments, an immunogenic amount of the passenger molecule, the modified MVP R8 protein, and/or the vault particle is administered to the subject. In some embodiments, the subject is human.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

The color versions of the drawings can be obtained in U.S. Application No. 62/579,303, filed Oct. 31, 2017. This invention is further understood by reference to the drawings wherein.

DETAILED DESCRIPTION OF THE INVENTION

Figure 16:
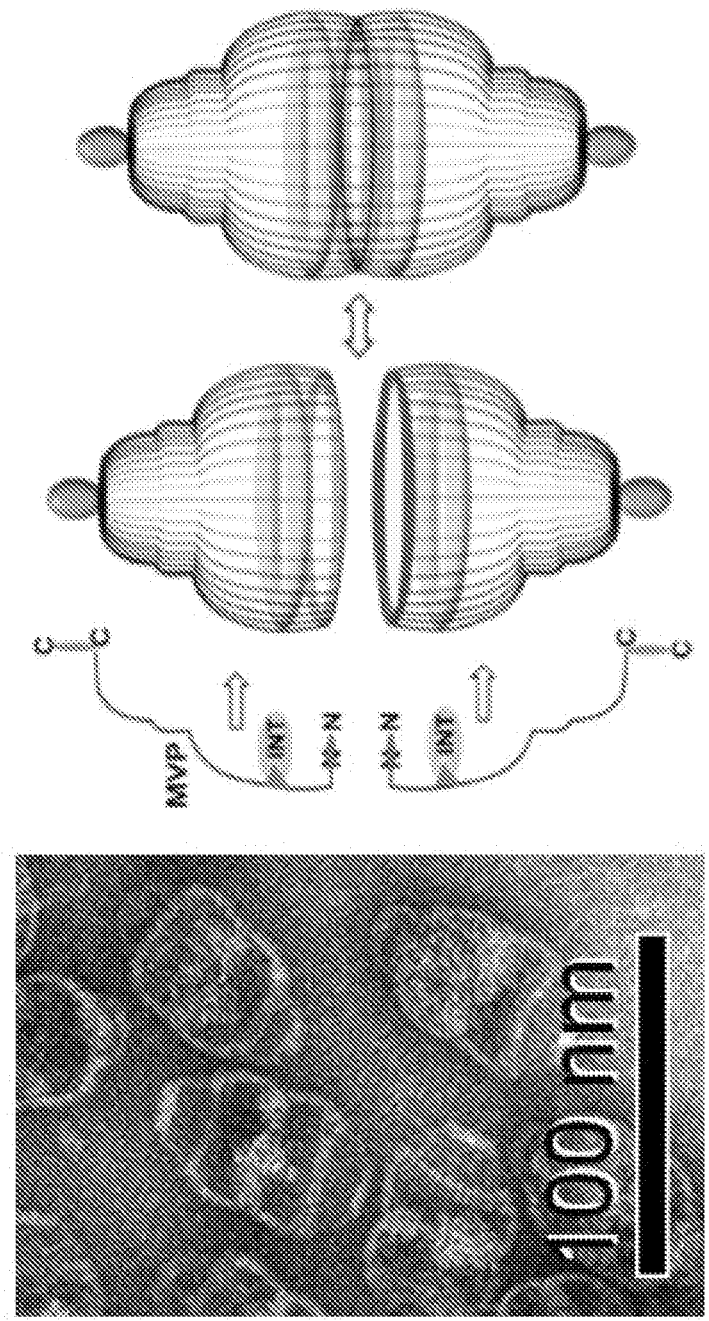
FIG. 16: Human recombinant vaults and vault structure. Left: Recombinant human vaults. Right: Structure of the vault shell, comprised of the major vault protein (MVP) in 78 repeating units, with N-termini facing inside the vault at the waist, C-termini at the outer poles, and an mINT passenger molecule.

Naturally occurring vaults comprise multiple copies of a major vault protein (MVP), tightly arranged to form a macromolecular structure having an ovoid shape with an interior cavity (referred to herein as a "barrel-like shape"). Each MVP is symmetrically arranged with the N-terminus at the waist of the particle and the C-terminus at the cap as shown in FIG. 16. Inside the shells of naturally occurring vaults are multiple copies of VPARP proteins and TEP1 proteins and multiple copies of one or more small vault RNAs (vRNAs) may also be present in naturally occurring vaults.

As used herein, the terms "vault" and "vault particle" are used interchangeably to refer to a ribonucleoprotein (RNP) comprising complexes of MVP proteins, alone or in combination with VPARP proteins and/or TEP1 proteins. Vault particles can be naturally occurring or synthetically made.

As used herein, "recombinant vaults", "engineered vaults", "recombinant vault particles", and "engineered vault particles" are used interchangeably to refer to vaults that have been synthesized using laboratory techniques, e.g., recombinant methods, as opposed to naturally occurring vaults. In some embodiments, recombinant vaults have a barrel-like shape that is the same as or substantially similar to naturally occurring vaults. Recombinant vaults, unlike naturally occurring vaults, do not necessarily comprise ribonucleic acid (RNA). That is, recombinant vaults may consist of a plurality of a given MVP protein (including modified MVP R8 proteins and fusion MVP R8 proteins). Recombinant vaults may comprise, in addition to the given MVP protein, one or more passenger molecules (see, e.g., [0046] to [0049]), a VPARP protein, and/or a TEP1 protein.

As used herein, an "MVP protein" refers to a protein that has at least about 85%, preferably about 90-100%, more preferably about 95-100%, and most preferably 97-100% sequence identity to a major vault protein and can form a part of a vault. Examples of major vault proteins are provided in the NCBI protein database (available on the Internet, ncbi.nlm.nih.gov/protein) and include GI: 41055865 (rat, NP_073206.2), GI: 239052674 (mouse, NP_542369.2), and GI: 15990478 (human, AAH15623.1, herein referred to as "human MVP"). In some embodiments, the MVP protein has at least about 85%, preferably about 90-100%, more preferably about 95-100%, and most preferably 97-100% sequence identity sequence identity to human MVP. MVP proteins can be synthetic, mutated, modified, human, animal (e.g., rat MVP), etc. In some embodiments, the MVP protein is an analog of human MVP. In some embodiments, the MVP protein is a homolog of human MVP. As used herein, "analogs" refer to proteins (or nucleic acid molecules) of heterologous origins that display the same or substantially similar activity. As used herein, "homologs" refer to proteins (or nucleic acid molecules) of a common origin, but do not necessarily exhibit the same or substantially similar activity.

As used herein, a "VPARP protein" refers to a protein that has at least about 85%, preferably about 90-100%, more preferably about 95-100%, and most preferably 97-100% sequence identity to a vault poly ADP-ribose polymerase and can form a part of a vault. Examples of VPARP proteins are provided in the NCBI protein database (available on the Internet, ncbi.nlm.nih.gov/protein) and include GI: 149064059 (rat, EDM14329.1), GI: 281485553 (mouse, NP_001139450.2), and GI: 112789550 (human, NP_006428.2). VPARP proteins can be synthetic, mutated, modified, human, animal (e.g., rat VPARP), etc. As used herein, an "mINT sequence" refers to the major vault protein interaction domain (mINT, also referred to as the "minimal interaction domain") of a given VPARP protein.

As used herein, a "TEP1 protein" refers to a protein that has 90-100%, preferably 95-100%, sequence identity to a telomerase/vault associated protein 1 and can form part of a vault. Examples of TEP1 proteins are provided in the NCBI protein database (available on the Internet, ncbi.nlm.nih.gov/protein) and include GI: 12018250 (rat, NP_072113.1), GI: 6678285 (mouse, NP_033377.1), and GI: 21536371 (human, NP_009041.2). TEP1 proteins can be synthetic, mutated, modified, human, animal (e.g., rat TEP1), etc.

As used herein, "passenger molecules" refer to molecules of interest that are carried on the surface of vault particles, molecules enclosed in vault particles (e.g., when vault particles are fully closed), molecules contained within the cavities of vault particles (e.g., when vault particles have openings or are partially formed), and molecules incorporated in the structures of vaults (e.g., covalently attached to the MVP proteins of vaults). In some embodiments, the passenger molecule is a protein (or fragment thereof), which is referred to herein as a "passenger peptide" or "passenger protein". In some embodiments, the passenger molecule is heterologous to its carrier molecule (e.g., heterologous to the vault particle containing the passenger molecule, heterologous to the mINT sequence or MVP protein that the passenger molecule is covalently attached to, etc.). In some embodiments, the passenger molecule is covalently linked to its carrier molecule using methods, e.g., recombinant techniques, in the art. In some embodiments, the passenger molecule is covalently linked to its carrier molecule using a linker, e.g., a flexible amino acid linker, in the art.

As used herein, an "mINT passenger molecule" refers to a passenger molecule that is covalently linked to an mINT sequence.

As used herein, an "N-linked passenger molecule" refers to a passenger molecule that is covalently linked to the N-terminus of an MVP protein, which may or may not be a fusion MVP R8 protein.

As used herein, an "C-linked passenger molecule" refers to a passenger molecule that is covalently linked to the C-terminus of an MVP protein, which may or may not be a fusion MVP R8 protein.

As used herein, "mINT fusion packaging" refers to a method where one or more mINT passenger molecules are mixed with formed vaults to thereby package the fusion molecules in the interior cavities of vaults (e.g., US 20120213809).

As used herein, "passive packaging" refers to a method where one or more passenger molecules are mixed with MVP proteins as they are being folded into vault structures having an interior cavity (e.g., WO 2016/049122). As used herein, "passively packaged passenger molecules" refer to a passenger molecule that has been packaged in the interior cavity of a vault particle by passive packaging.

As used herein, a "modified R8 vault" refers to a vault particle comprising an MVP protein having an R8 flexible region that has been synthetically modified, e.g., by recombinant techniques, to contain at least one amino acid substitution, deletion, or addition, e.g., a modified MVP R8 protein or a fusion MVP R8 protein as described herein. In some embodiments, the present invention is directed to a modified R8 vault. In some embodiments, modified R8 vaults have a barrel-like shape that is the same as or substantially similar to naturally occurring vaults.

As used herein, a "modified MVP R8 protein" refers to an MVP protein that contains a modified R8 flexible region as described herein. Modified MVP R8 proteins include fusion MVP R8 proteins. In some embodiments, the present invention is directed to a modified MVP R8 protein.

As used herein, a "fusion MVP R8 protein" refers to an MVP protein having a passenger molecule (preferably a passenger peptide), which is heterologous to the MVP protein, covalently linked to its R8 flexible region as described herein or its modified R8 flexible region as described herein. In some embodiments, the present invention is directed to a fusion MVP R8 protein. In some embodiments, the passenger molecule is covalently linked at or near the N-terminus of the R8 flexible region or the modified R8 flexible region. In some embodiments, the passenger molecule is covalently linked at or near the C-terminus of the R8 flexible region or the modified R8 flexible region. In some embodiments, the passenger molecule is covalently linked at or near the middle of the R8 flexible region or the modified R8 flexible region. In some embodiments, the passenger peptide comprises up to about 260 amino acid residues. In some embodiments, the passenger peptide comprises up to about 255 amino acid residues. In some embodiments, the passenger peptide comprises up to about 250 amino acid residues. In some embodiments, the passenger peptide comprises up to about 245 amino acid residues. In some embodiments, the passenger peptide comprises up to about 240 amino acid residues. In some embodiments, the passenger peptide comprises up to about 236 amino acid residues. Because the diameter of the space in the area of the R8 flexible region of MVP is about 30 Å, in some embodiments, the passenger molecule inserted in the R8 flexible region has a three-dimensional globular size of up to about 30 Å. In some embodiments, the fusion MVP R8 protein may further comprise one or more additional passenger molecules covalently linked to the N-terminus and/or the C-terminus of the MVP protein.

As disclosed herein, cryo-electron microscopy (cryoEM) and single particle analysis were performed on vault particles at near-atomic resolution (about 4.8 Å). The vault particles were recombinantly engineered to contain a portion of HIV-1 Gag (amino acids 148-214) covalently attached to the N-terminus of an MVP protein. Examination of the structure of the recombinant vault particles led to the hypothesis that vault particles contain a region in the R8 domain of each MVP protein that can be modified to contain passenger molecules without negatively disrupting the formation of the barrel-like structure of vault particles. These regions in the R8 domains are referred to herein as "R8 flexible regions".

The R8 flexible region of human MVP comprises the amino acids from about the $428^{th}$ amino acid residue to about the $449^{th}$ amino acid residue of human MVP. The amino acid sequence of human MVP from amino acids 428-449 is NKGQDPLADRGEKDTAKSLQPL (SEQ ID NO: 3). The R8 flexible region of an MVP protein other than human MVP comprises the amino acids of the MVP protein that correspond to about the $428^{th}$ amino acid residue to about the $449^{th}$ amino acid residue of human MVP. In some embodiments, the amino acids of a given MVP protein that correspond to the $428^{th}$ amino acid residue to the $449^{th}$ amino acid residue of human MVP are the amino acid residues that align with amino acid residues 428-449 of human MVP when the sequence of the given MVP protein is optimally aligned with the human MVP sequence using methods in the art. See, e.g., paragraph [0081] below. In some embodiments, the amino acids of a given MVP protein that correspond to the $428^{th}$ amino acid residue to the $449^{th}$ amino acid residue of human MVP are the amino acid residues that map to amino acid residues 428-449 of human MVP using protein modeling methods in the art. See, e.g., Kufareva, I., & Abagyan, R. (2012) Methods of protein structure comparison. Methods in Molecular Biology (Clifton, N.J.), 857:231-257. In some embodiments, the R8 flexible region of a given MVP protein is about 15 to about 32 amino acid residues in length. In some embodiments, the R8 flexible region of the given MVP protein is 15 amino acid residues in length. In some embodiments, the R8 flexible region of the given MVP protein is 16 amino acid residues in length. In some embodiments, the R8 flexible region of the given MVP protein is 17 amino acid residues in length. In some embodiments, the R8 flexible region of the given MVP protein is 18 amino acid residues in length. In some embodiments, the R8 flexible region of the given MVP protein is 18 amino acid residues in length. In some embodiments, the R8 flexible region of the given MVP protein is 19 amino acid residues in length. In some embodiments, the R8 flexible region of the given MVP protein is 20 amino acid residues in length. In some embodiments, the R8 flexible region of the given MVP protein is 21 amino acid residues in length. In some embodiments, the R8 flexible region of the given MVP protein is 22 amino acid residues in length. In some embodiments, the R8 flexible region of the given MVP protein is 23 amino acid residues in length. In some embodiments, the R8 flexible region of the given MVP protein is 24 amino acid residues in length. In some embodiments, the R8 flexible region of the given MVP protein is 25 amino acid residues in length. In some embodiments, the R8 flexible region of the given MVP protein has at least about 70%, preferably about 75-100%, more preferably about 80-100%, even more preferably about 85-100%, and most preferably about 90-100% sequence identity to VEELLNKGQDPLADRGEKDTAKSLQPLAPRNK (SEQ ID NO: 4) when optimally aligned thereto. In some embodiments, the R8 flexible region of the given MVP protein has at least about 70%, preferably about 75-100%, more preferably about 80-100%, even more preferably about 85-100%, and most preferably about 90-100% sequence identity to NKGQDPLADRGEKDTAKSLQPL (SEQ ID NO: 3) when optimally aligned thereto.

As used herein, a "modified R8 flexible region" refers to an R8 flexible region that has been synthetically modified, e.g., using recombinant techniques, to contain one or more amino acid substitutions, additions, and/or deletions. In some embodiments, the modified R8 flexible region is about 2 to about 32 amino acid residues in length. In some embodiments, the modified R8 flexible region is about 2-5 amino acid residues in length. In some embodiments, the modified R8 flexible region is about 5-10 amino acid residues in length. In some embodiments, the modified R8 flexible region is about 10-15 amino acid residues in length.

In some embodiments, the modified R8 flexible region is 15 amino acid residues in length. In some embodiments, the modified R8 flexible region is 16 amino acid residues in length. In some embodiments, the modified R8 flexible region is 17 amino acid residues in length. In some embodiments, the modified R8 flexible region is 18 amino acid residues in length. In some embodiments, the modified R8 flexible region is 18 amino acid residues in length. In some embodiments, the modified R8 flexible region is 19 amino acid residues in length. In some embodiments, the modified R8 flexible region is 20 amino acid residues in length. In some embodiments, the modified R8 flexible region is 21 amino acid residues in length. In some embodiments, the modified R8 flexible region is 22 amino acid residues in length. In some embodiments, the modified R8 flexible region is 23 amino acid residues in length. In some embodiments, the modified R8 flexible region is 24 amino acid residues in length. In some embodiments, the modified R8 flexible region is 25 amino acid residues in length. In some embodiments, the modified R8 flexible region has about 70-99%, preferably about 75-99%, more preferably about 80-99%, even more preferably about 85-99%, and most preferably about 90-99% sequence identity to VEELLNKGQDPLADRGEKDTAKSLQPLAPRNK (SEQ ID NO: 4) when optimally aligned thereto. In some embodiments, the modified R8 flexible region has about 70-99%, preferably about 75-99%, more preferably about 80-99%, even more preferably about 85-99%, and most preferably about 90-99% sequence identity to NKGQDPLADRGEKDTAKSLQPL (SEQ ID NO: 3) when optimally aligned thereto.

Figure 15:
FIG. 15: Modification of the R8 flexible region nucleic acid sequence to create a restriction site for rapid insertion of cargo protein sequences. The coding sequence for the human R8 flexible region (human MVP amino acids 428-449) is shown, and the point of insertion of a restriction enzyme (AfeI) cutting site is indicated. The first three nucleotides and the last three nucleotides are nucleotides that flank the R8 flexible region. The top sequence is SEQ ID NO: 1 and the bottom sequence is SEQ ID NO: 2.

Further experiments confirmed this hypothesis. Specifically, short HIV sequences and mCherry (Shaner, et al., 2004) ranging from were inserted into the R8 flexible region of human MVP via PCR mutagenesis and the vault particles formed therefrom exhibited normal morphology, i.e., barrel-like structures that are indistinguishable from recombinant vaults formed from unmodified human MVP. Thus, a passenger peptide comprising up to about 260 amino acid residues can be packaged into the interior cavity of vault particles without disrupting the formation of the barrel-like structure. Because the diameter of the space in the area of the R8 flexible region of MVP is about 30 Å, in some embodiments, the passenger molecule inserted in the R8 flexible region has a three-dimensional globular size of up to about 30 Å. Additionally, as described herein, a modified MVP R8 protein was made using PCR mutagenesis to insert a restriction enzyme site into the nucleic acid sequence of human MVP that encodes the R8 flexible region (FIG. 15) and recombinant vaults formed therefrom also exhibited normal morphology.

Therefore, in some embodiments, the present invention provides recombinant vault particles that comprise a modified MVP R8 protein. In some embodiments, the nucleic acid sequence encoding the R8 flexible region of a given MVP protein has been modified to contain a restriction enzyme site or an adapter sequence, whereby, for example, a nucleic acid molecule encoding a passenger peptide can be readily inserted therein using recombinant techniques. In some embodiments, the present invention provides methods of packaging a passenger molecule into the interior cavity of a vault particle, which comprises recombinantly inserting the passenger molecule into the R8 flexible region of an MVP protein of the vault particle. In some embodiments, a flexible linker (e.g., GGGGSGGGGSGGGGS (SEQ ID NO: 5)) is inserted at one or both ends of the passenger molecule to minimize the likelihood of steric hinderance.

Based on the results of the cryoEM experiments described herein, passenger molecules inserted in the R8 flexible region will likely result in the payload being divided between the top and bottom halves and away from the waist of the barrel-like structure. Thus, passenger molecules inserted in the R8 flexible region of an MVP protein should have a smaller impact, if any, on the formation of the barrel-like structure as compared to the MVP protein having a passenger molecule covalently attached to its N-terminus.

Because a passenger molecule inserted in the R8 flexible region will be located away from the waist of the vault particle, a second passenger molecule may be packaged within the vault cavity by covalently attaching it to the N-terminus of the MVP protein (having the first passenger molecule inserted in the R8 flexible region), by methods in the art, e.g., recombinant techniques. In some embodiments, a vault particle having a passenger molecule inserted in the R8 flexible region of an MVP protein contain second passenger molecule covalently attached to the C-terminus of the MVP protein (having the first passenger molecule inserted in the R8 flexible region). In some embodiments, a vault particle having a passenger molecule inserted in the R8 flexible region of an MVP protein contain second passenger molecule packaged in the interior cavity of the vault particle by mINT fusion packaging and/or by passive packaging.

Vaults have Multiple Conformations in Solution

Figure 1:
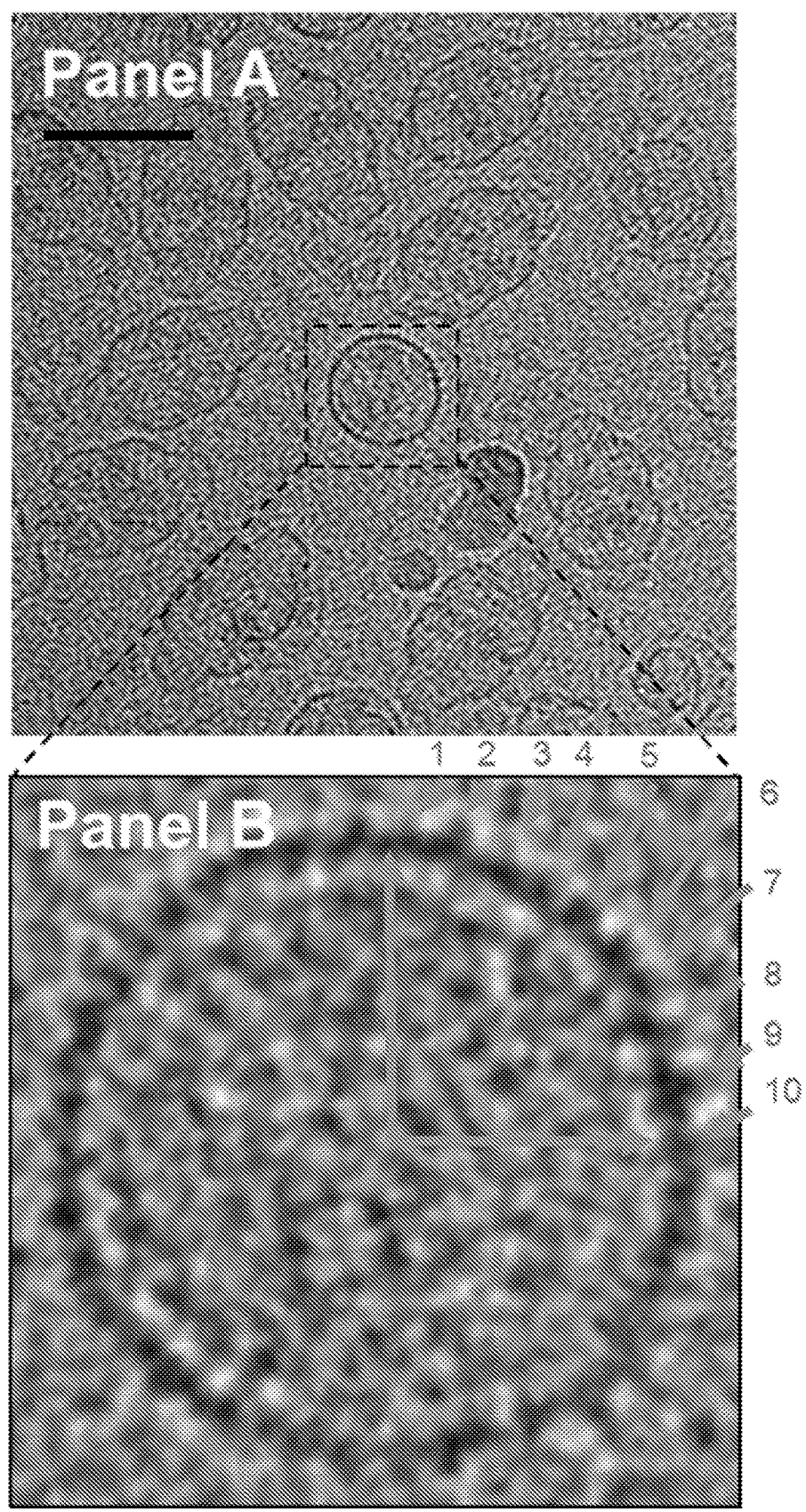
FIG. 1: CryoEM single particle analysis result on engineered MVP-only vault. Panel A) Aligned sum of rat vault raw image stack, showing this dataset has nice orientation distribution. Typical top views are boxed in black square. The scale bar is 50 nm. Panel B) Magnified raw image of top view to show there are about 10 copies in a quadrant of circle, implying close to 40-fold related symmetry.

To enhance image contrast and to help clarify the number of MVP monomers/vault, movies of recombinant rat vaults embedded in vitreous ice in a Titan Krios 300 kV electron microscope equipped with a K2 Summit direct electron-counting detector were recorded. Though vaults appeared mostly in their side views in the movies, occasionally top views of the vault can be spotted, showing features that indicate the separation of individual MVP monomers (e.g., one MVP monomer on the top half of the vault closer to the viewer and the other on the bottom half) lining along the direction of the view (FIG. 1, Panel A). The number of MVP pairs within one of the four quadrants of the top view (FIG. 1, Panel B) is between 9 and 10, consistent with 39 MVP pairs (e.g., 78 MVP monomers/vault, as in PDB 4HL8 and 4V60) (Casanas et al., 2013; Tanaka et al., 2009), but different from those used in other studies, such as PDB 2QZV (96 MVP monomers/vault) (Anderson et al., 2007).

Figure 2:
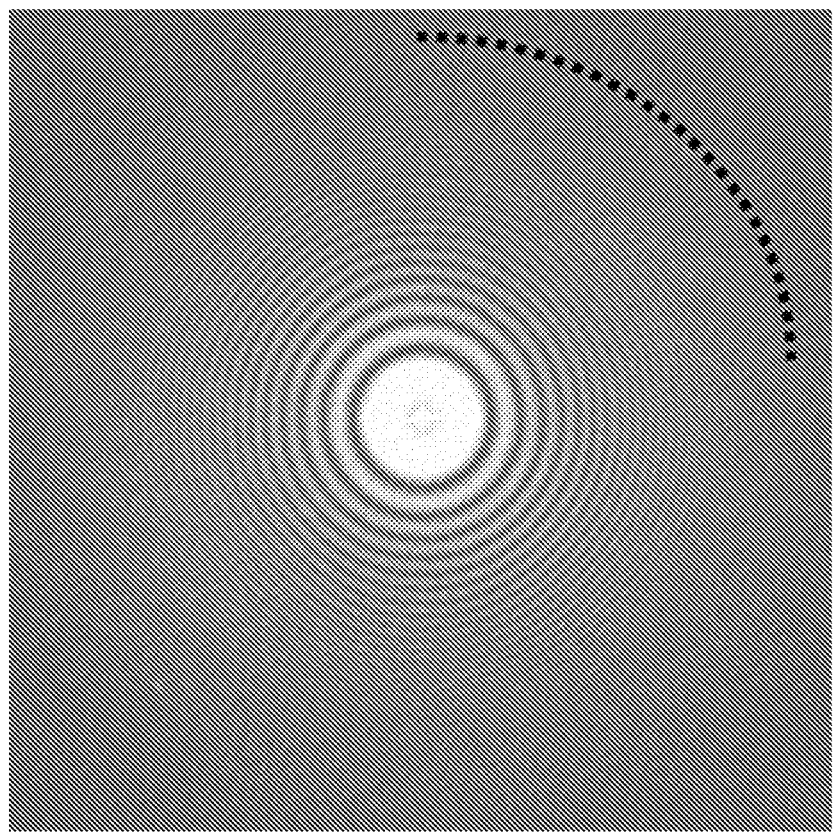
FIG. 2: Fourier transform of a sum micrograph. Thon rings can reach to water signal at close to 3.6 Å-1.
Figure 13:
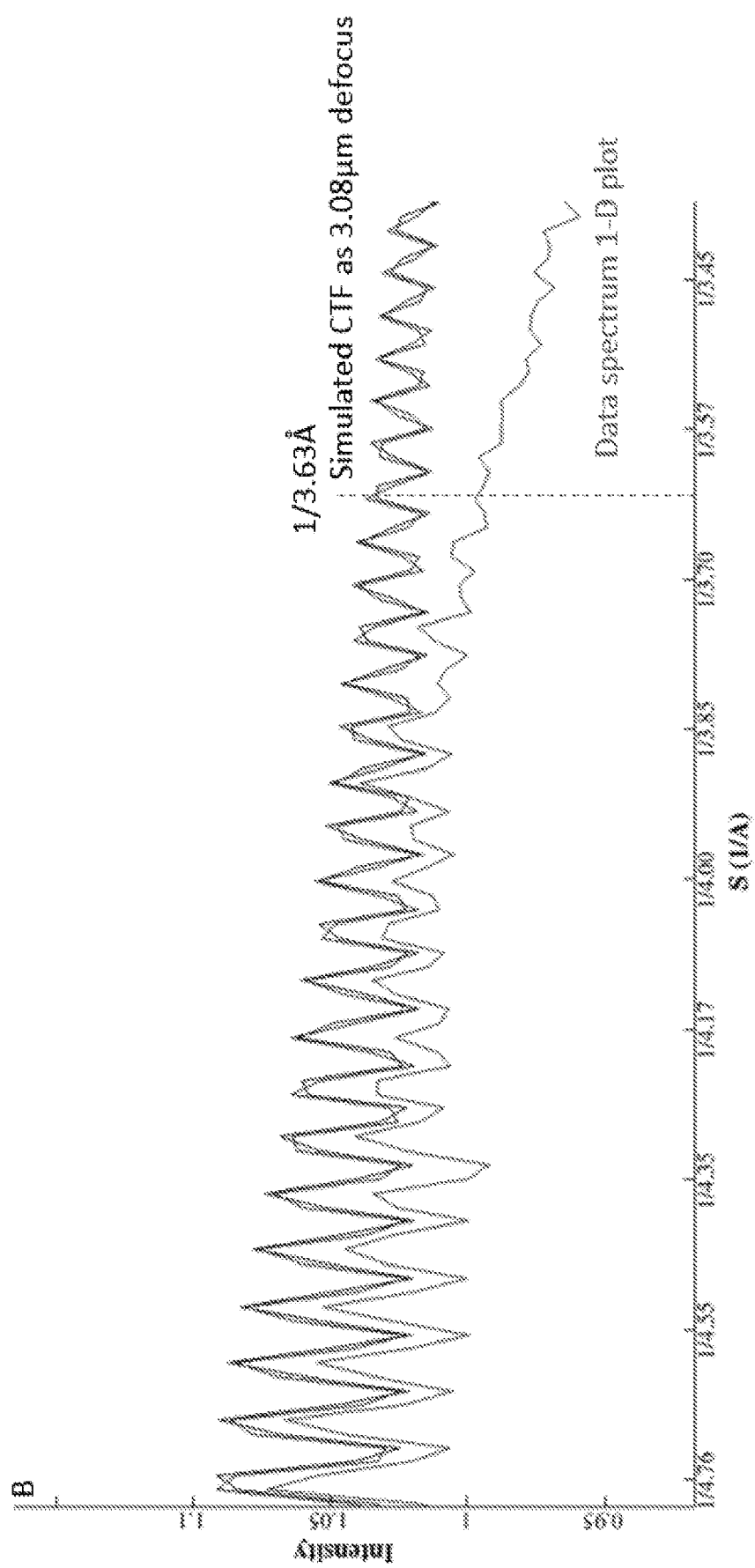
FIG. 13: Data validation. 1-D plot of a raw micrograph shows that signal is transferred to atomic resolution.

The power spectrum of drift-corrected images shows that the Thon rings extend to $1/3.6$ Å$^{-1}$ (FIG. 2 and FIG. 13), indicating that the images have structural information beyond 3.6 Å resolution. However, the best resolution achieved after exhaustive attempts to carry out single-particle reconstruction by Frealign (Lyumkis et al., 2013) was only 13.5 Å. This structure did not resolve individual MVP monomers at the cap region, hence the handedness of the reconstruction could not be established. This observation suggests existence of multiple conformations in the sample. To sort out multiple conformations, three-dimensional (3D) classification with Relion (Scheres, 2012) following the scheme illustrated in FIG. 14 was subsequently performed.

Figure 3:
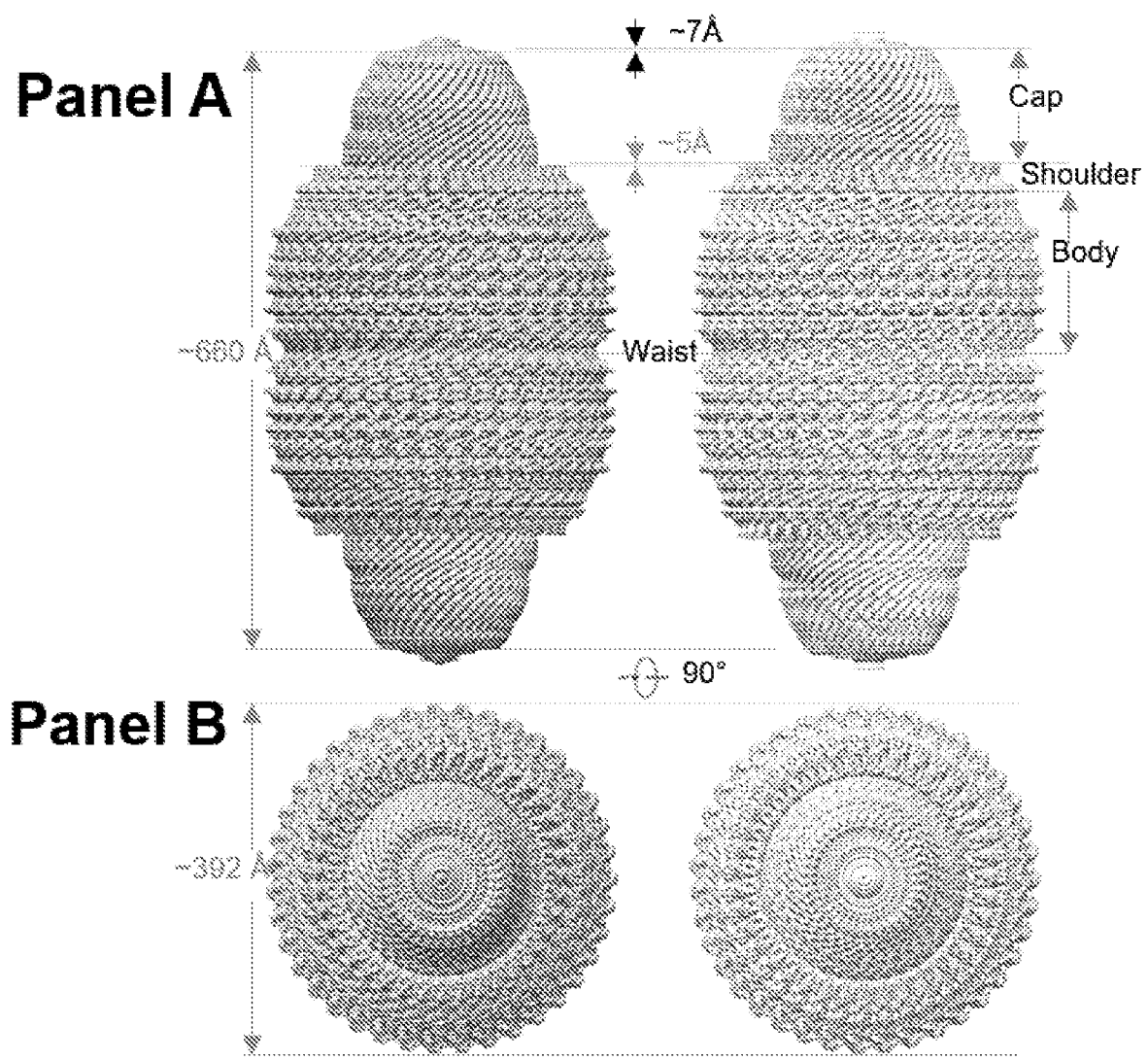
FIG. 3: Density map of two vault conformations refined from a single dataset. Panel A) Conformation 1 (displayed at 4.4 σ) is in pink and conformation 2 (displayed at 4.5 σ) is in yellow. They are all in D39 symmetry. Panel B) Top view of vault density in Panel A. No diameter change can be observed.
Figure 4:
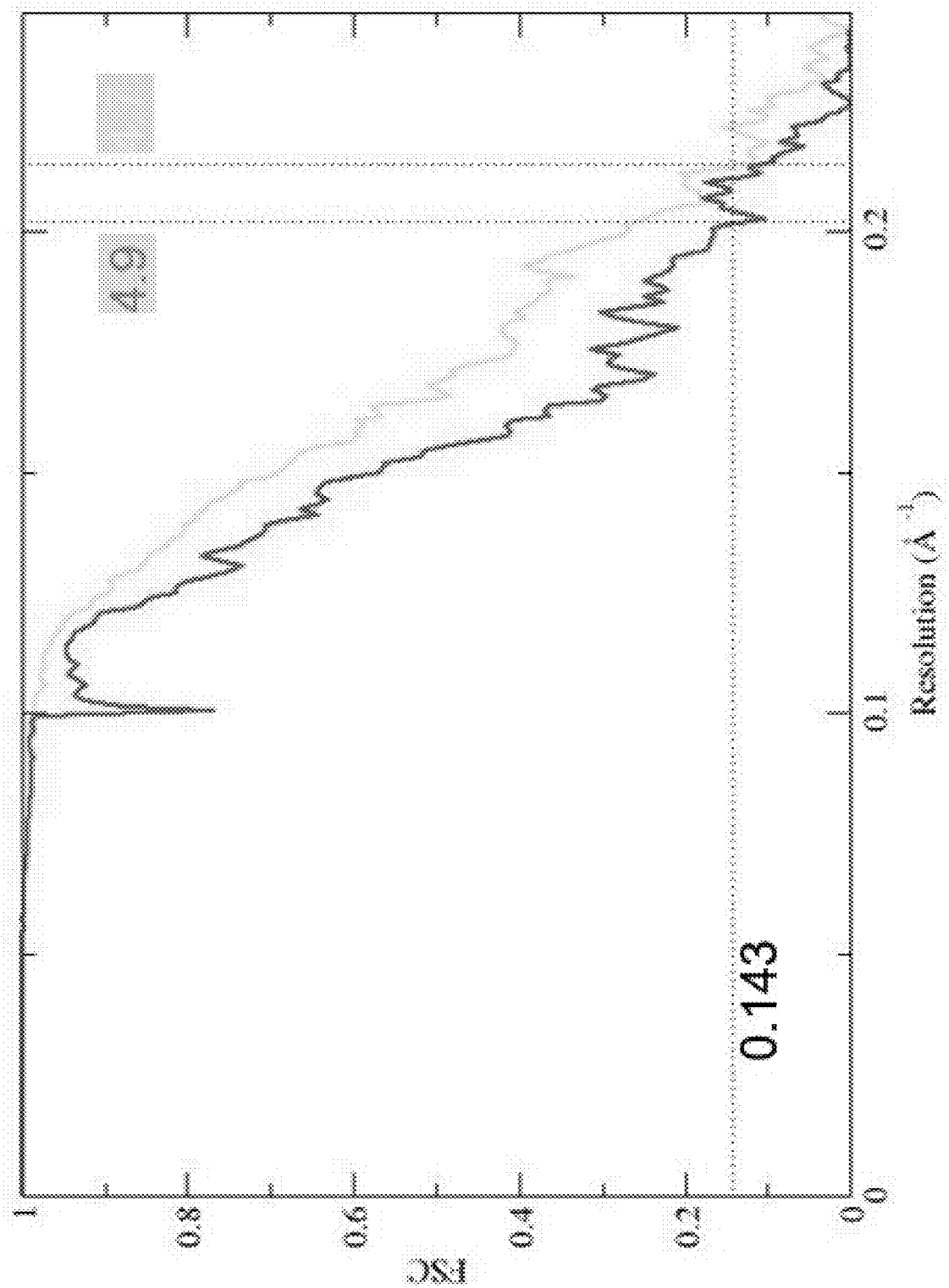
FIG. 4: FSC curve showing that the resolution (FSC 0.143) of the two conformations are 4.9 Å and 4.7 Å, respectively.
Figure 5:
FIG. 5: Structural comparison of conformation 1 (purple) and corresponding model, and conformation 2 (olive) and corresponding model.
Figure 6:
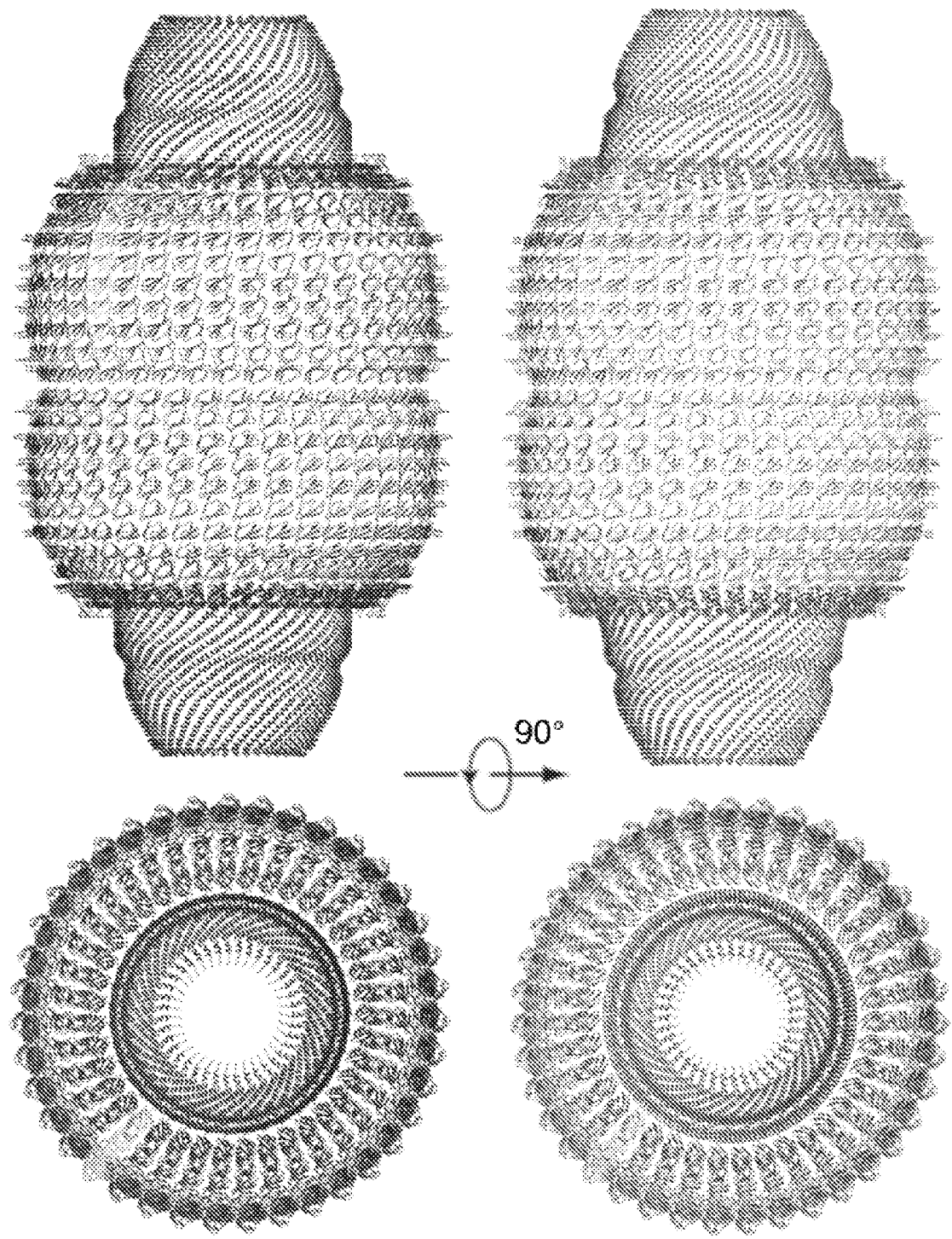
FIG. 6: Model comparison between conformation 1 (purple) and conformation 2 (olive). One copy of major vault protein (MVP) is colored in rainbow. The back half is hidden for clarity.
Figure 7:
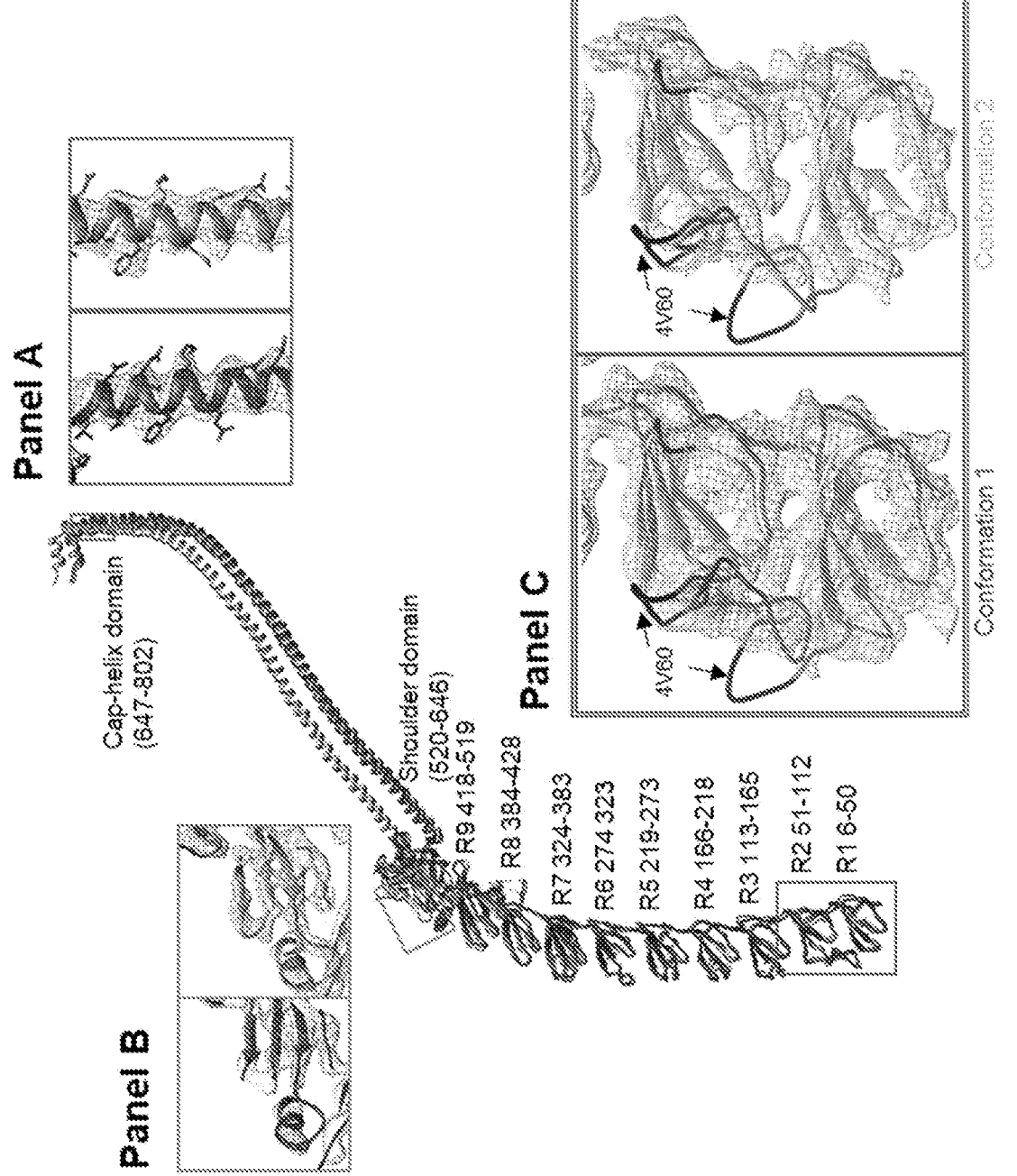
FIG. 7: Overlapped model comparison. R1-R7 has no major conformational change. PDB 4HL8 is colored in aqua to show similarities between conformation 1 model and PDB 4HL8. Near-atomic resolution feature at shoulder and cap-helix domain in both conformations, including an α-helix (Panel A) and β-sheet (Panel B). Large side chains can be identified and is consistent with current resolution estimation. Contour displayed at 6.7 σ. Panel C) Magnified view at R1 and R2 domain of two conformations. 4V60 model (grey) are displayed. The mismatch region in 4V60 is colored with black. No significant flexible region can be found at R1 and R2 domain. The major conformational change of cryoEM vault structure is not at waist region. Mesh contour is displayed at 5 σ for conformation 1 (pink) and 6.4 σ for conformation 2 (yellow).

Reconstructions with D38 or D40 symmetry did not converge to structures resolving any detailed features to establish handedness in the cap, even after exhaustive 3D classification and refinement. By contrast, reconstruction with D39 symmetry yielded two structure classes (i.e., conformations) that both converged to near atomic resolution (4.9 Å for conformation 1 and 4.7 Å for conformation 2) (FIG. 3, Panels A and B, and FIG. 4). Both conformations reveal extensive secondary structures and some bulky side chains of amino acid residues (FIG. 5, FIG. 6, and FIG. 7, Panel A).

In these two conformations, the two halves of the barrel-shaped vault are joined at the waist. Extending away from the waist to the distal end of the vault are the body, the shoulder, and the cap regions of each half (FIG. 3, Panel A). Similar to previously reported vault X-ray structures (Casanas et al., 2013; Tanaka et al., 2009), 39 MVP monomers line in parallel to form half of the vault. The top center of cap region is closed with no discernable features in our D39-symmetry-imposed maps, indicating that the D39 symmetry is not maintained in this location (FIG. 3, Panel B).

While conformation 1 and conformation 2 have the same waist radius, conformation 2 is 14 Å longer than conformation 1 along the D39 symmetry axis direction (FIG. 3, Panel A). This observation suggests that the conformational changes are real and not an artifact of display differences or magnification variation in the microscope. This is the first direct evidence that two distinct vault conformations exist in solution.

Engineered MVP-Only Vaults can Adopt the Structure of Naturally-Occurring Vaults The availability of the crystal structure of naturally-occurring vaults (Casanas et al., 2013) (PDB 4HL8) allowed the interpretation of the cryoEM structures of conformation 1 and conformation 2 at moderate resolutions of 4.9 and 4.7 Å, respectively. Consistent with crystal structure PDB 4HL8, the cryoEM densities of MVP monomers in both conformation 1 and conformation 2 reveal the characteristic 9 repeats (R1 through R9) of β-sheet domains, followed by a shoulder domain with 4 α-helices and a 4-stranded β-sheet, and a long (about 230 Å) cap helix (FIG. 5 and FIG. 6). PDB 4HL8 can be fitted only into conformation 1 density as a rigid body, indicating that conformation 1 is very close to crystal structure PDB 4HL8.

Therefore, the PDB 4HL8 crystal structure was selected as the starting model for real-space refinement of the MVP monomer of conformation 1. The refinement result shows that it is nearly identical to PDB 4HL8 with a root-mean-square deviation (RMSD) value of 1.3 Å. The traceable region covers most of the vault body and cap side walls, including R1-R9, shoulder, cap-helix, and cap-ring domains (FIG. 5 and FIG. 7). The traceable sequence ends at P815 in the cap-ring domain. The rest of the density at the cap region is insufficiently resolved for reliable tracing of the C-terminal segment, from amino acid residues 816 to 861 (FIG. 3, Panel A and FIG. 6). Unlike naturally-occurring vaults, the recombinant vault particles analyzed herein do not contain TEP1, VPARP or vRNA, yet the density at the center of the cap top remains solid, suggesting that the density observed at the center of the cap top in the two cryoEM conformations do not exclusively correspond to TEP1, VPARP, or vRNA as previously suggested (Kong et al., 1999; Tanaka et al., 2009; Tanaka and Tsukihara, 2012).

Figure 8:
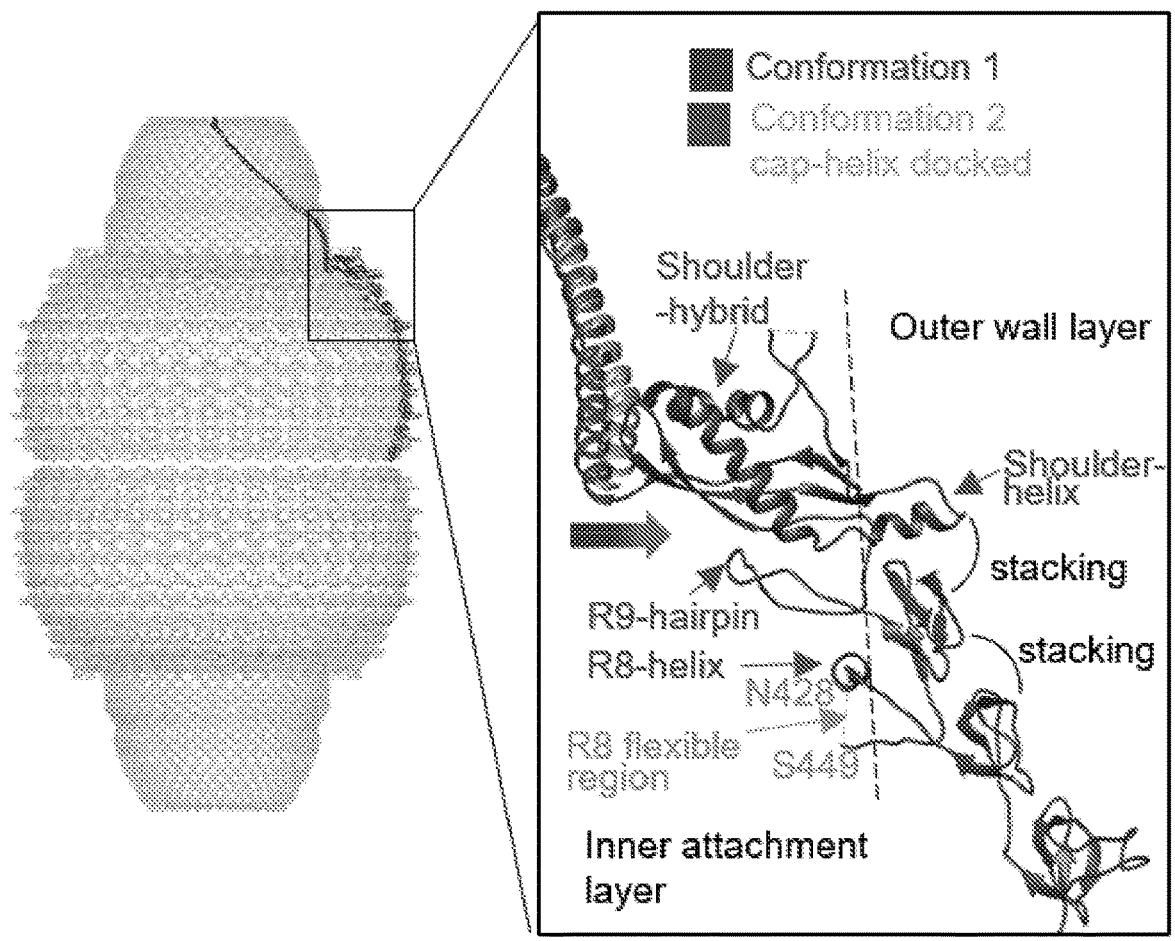
FIG. 8: Conformational change diagram. conformation 1 monomer model as a side view in vault over all model and magnified view of R7 to cap-helix domain. The R8 flexible region between N428 to S449 locates inside the vault. The docking of helix-cap domain of conformation 2 into conformation 1 density shows that cap-helix domain in conformation 2 bends outwards comparing with conformation 1. R8 to shoulder domain can all be roughly divided into two parts, separated by the dashed line. The attachment layer locates inside and the wall layer locates outside. The conformational studies were performed using rat MVP (the amino acid residue of human MVP that corresponds to S449 is L449).
Figure 12:
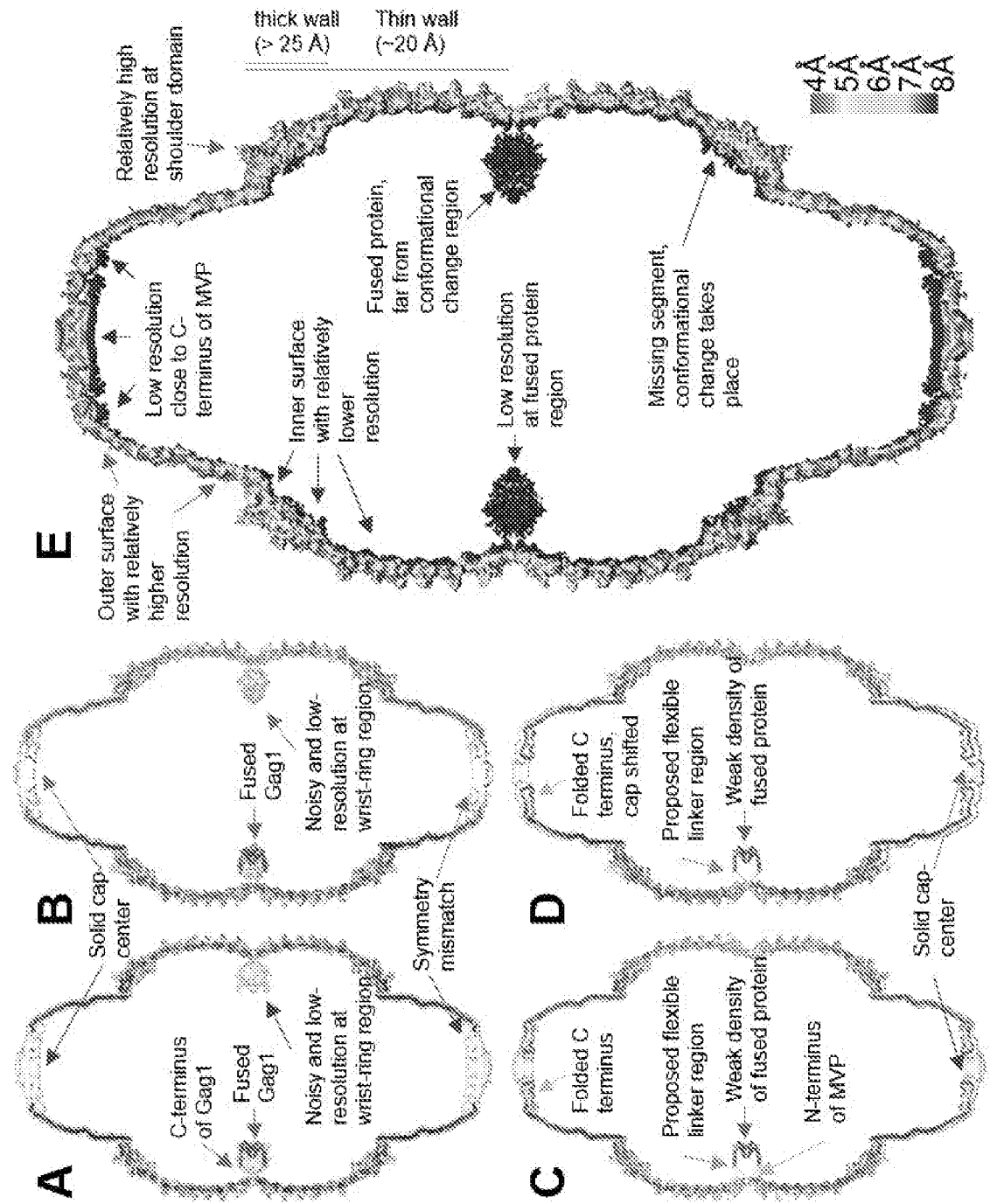
FIG. 12: Model and density comparison among models and densities via longitudinal section. Panel A) Conformation 1 model (purple), conformation 1 density (pink, displayed at 3 σ) and docked segmented Gag dimer (PDB 1AFV, red). Panel B) Conformation 2 model (olive), conformation 2 density (yellow, displayed at 3.7 σ) and docked Gag dimer (red). Panels C and D) utilizing similar color code with Panel A and Panel B, respectively, with higher visualization threshold (displayed 6.2 σ and 5.1 σ for conformation 1 and conformation 2, respectively). PDB 4V60 (grey) is docked into conformation 1 and conformation 2 density. C-terminus of Gag and N-terminus of MVP is connected by flexible linker, shown as dashed line. Panel E) Local resolution estimation of conformation 2 density map calculated by Resmap (Kucukelbir et al., 2014). The flexible region is of low resolution and appear blue (covalently attached protein at waist, C-terminus near cap and inner surface). The major conformational change takes place at shoulder domain but the resolution is relatively high.

At the waist region inside the vault is the Gag 148-214 peptide covalently attached to the N-terminus of MVP (FIG. 12, Panels A and C). The sectional view shows that the covalently attached Gag peptide is fully encapsulated inside the vault (FIG. 12, Panel A and C). The thickness of the vault shell varies: close to 20 Å from R1 through R7 domains and thicker than 25 Å from R8, R9, and the shoulder domains (FIG. 12, Panel E). R1 through R7 domains are also less structurally complex than R8, R9, and the shoulder domains. For example, in addition to the antiparallel β-sheet fold sub-domains of R8 and R9 (which resemble the antiparallel β-sheet fold in each of R1 through R7 domains), both the R8 and R9 domains contain an inner attachment sub-domain—an α-helix in R8 (R8-helix) and a hairpin in R9 (R9-hairpin) atop R8-helix (FIG. 8). The shoulder domain has folding motif different from the antiparallel β-sheet fold of R1 through R9 and can be roughly divided into two sub-domains: a shoulder-helix sub-domain next to R9's antiparallel β-sheet fold, and a shoulder-hybrid sub-domain (featuring a combination of α-helix and β-sheet) next to the inward-projecting R9-hairpin (FIG. 8). It is the presence of the inner-layer sub-domains in R8, R9, and shoulder domains that contributes to extra thickness of these domains as compared to R1 through R7 domains. The segment of the MVP monomer (amino acid residues N428 to S449 that connect R8 with R9) missing in previous X-ray crystal structures (Casanas et al., 2013; Tanaka et al., 2009) remained unresolved in cryoEM structure of conformation 1 (FIG. 8).

Conformation of Vaults on Solution

The local resolutions of most regions in the density map of conformation 2 are between 4 Å to 6 Å (FIG. 12, Panel E), with the best resolution in the R1-R9 and the shoulder and the lowest resolution in the folded C-terminal region at the cap and the covalently attached protein (Gag 148-214) at the waist. The resolution of the entire inner surface of the vault is lower than that of the outer surface. The elongation of MVP monomer towards the pole of the vault particle in conformation 2 prevented satisfactory fitting of PDB 4HL8 as a rigid body into the density. R1 through R7 domains in PDB 4HL8 fit well with conformation 2 density, however, the R8, R9, shoulder, cap-helix, and cap-ring domains do not. Thus, the atomic model for R1 through R7 domains of PDB 4HL8 was fitted into the conformation 2 map. To address the previous discrepancies at the waist region, PDB 4V60 was also docked into the density of conformation 2 to see if this earlier X-ray model could represent conformation 2 of the vault in solution. This docking revealed that R1 and R2 domains in PDB 4V60 do not match the cryoEM density of conformation 2 (FIG. 7, Panel C). This in combination with conformation 1 adopting the structure of PDB 4HL8 suggests that PDB 4V60 does not represent the conformation of the vault in solution.

The atomic model of individual α-helixes and β-sheets in R8, R9, shoulder domain, cap-helix domain, and cap-ring domain of PDB 4HL8 were fitted into their corresponding secondary structure elements visible in the cryoEM density map as rigid bodies. These fitted secondary structures were connected using linkers derived from the MVP sequence to create a full trial atomic model, which was subjected to model refinement against the cryoEM map. The resulting model (FIG. 5, olive) has a $C_\alpha$ RMSD value of 5.95 Å when compared with PDB 4HL8 as provided in Table 1:

TABLE 1

| Structural Statistics of the 2 Conformers | | | |
|---|---|---|---|
| Conformation ID | | # 1 | # 2 |
| B-factor for map (Å$^2$) | | −160 | −225.5 |
| MapCC (around atoms) | | 0.761 | 0.752 |
| Phenix RMSD | Bond (Å) | 0.0026 | 0.0033 |
| | Angles | 0.68 | 0.81 |

TABLE 1-continued

Structural Statistics of the 2 Conformers

| Conformation ID | | # 1 | # 2 |
|---|---|---|---|
| Ramachandran plot (from | Outliers | 1.16% | 1.17% |
| Phenix) | Allowed | 4.12% | 4.83% |
| | Favored | 94.72% | 93.99% |
| All atom clash score | | 10.53 | 13.71 |
| Cα RMSD Value to PDB 4HL8 | | 1.3 Å | 5.95 Å |
| Rotamer outliers | | 0.00% | 0.00% |
| C-beta deviation | | 0 | 0 |

Figure 9:
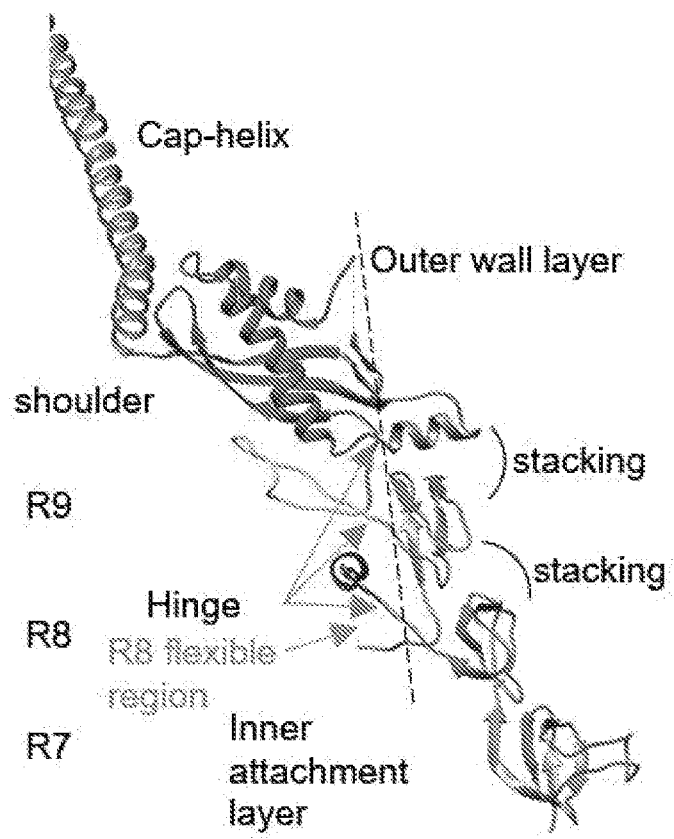
FIG. 9: R7 to cap-helix domain of conformation 2. Like conformation 1, the R8 to shoulder domain is double layered. The inner-layer is colored from blue to red, from N-terminus to C-terminus. The outer layer is colored in original olive color.
Figure 10:
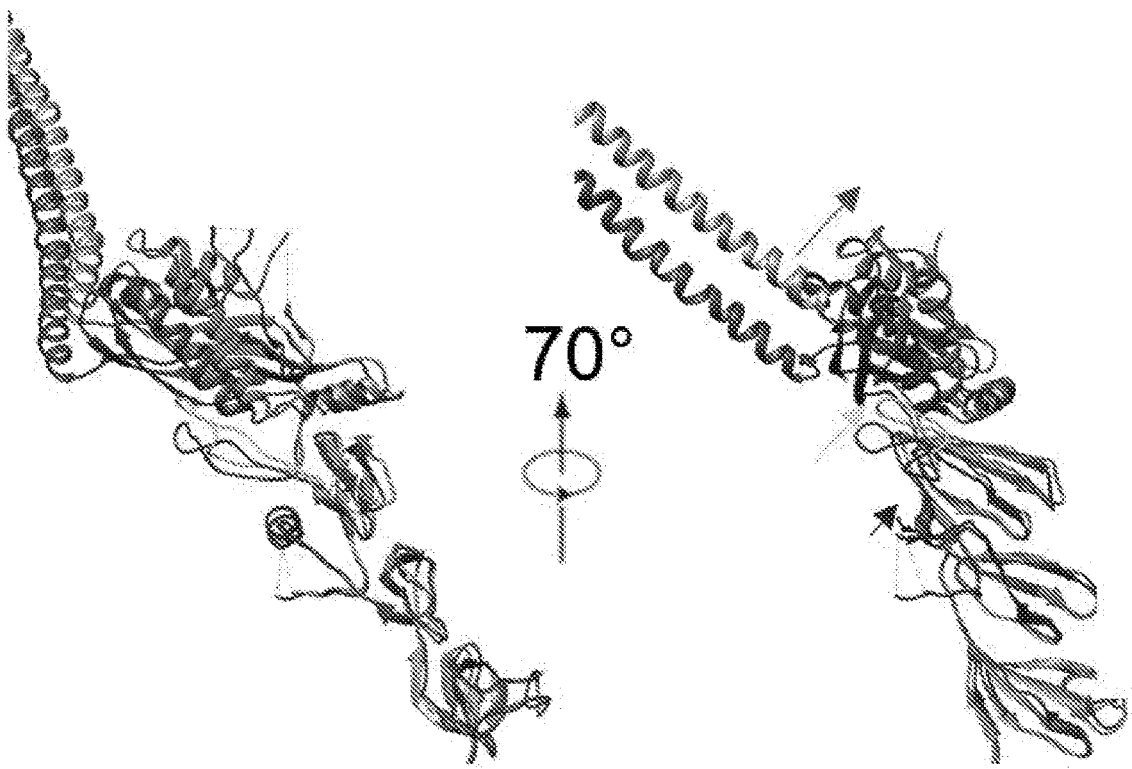
FIG. 10: Direct overlapping of conformation 1 and conformation 2 model. Position shift is magnified from R8 to shoulder domain. The relative movement of attachment layer is labeled with corresponding color and the movement is larger from R8 to shoulder domain.

The conformational changes in the refined model of conformation 2 take place at the R8 domain (P420) and become larger as one moves toward the C terminus (FIG. 7). R8 and R9 domains undergo minor conformational changes by slightly bending outwards, pivoting around their respective N-termini. Like that in conformation 1, the structure of the MVP segment from amino acid residues N428 to S449 in conformation 2 could not be resolved. Nevertheless, the unresolvable segment likely occupies a space within the cavity of the vault particle near the inner surface of the R8 and R9 domains (FIG. 9, labeled "R8 flexible region"). In general, while the secondary structure elements in R8 and R9 domains are conserved between conformation 1 and conformation 2, the relative positions of these secondary structure elements and their connecting linkers are not. Compared that in conformation 1, the shoulder domain in conformation 2 is twisted further outward, along with the attached cap-helix domain (FIG. 7 and FIG. 10).

Figure 11:
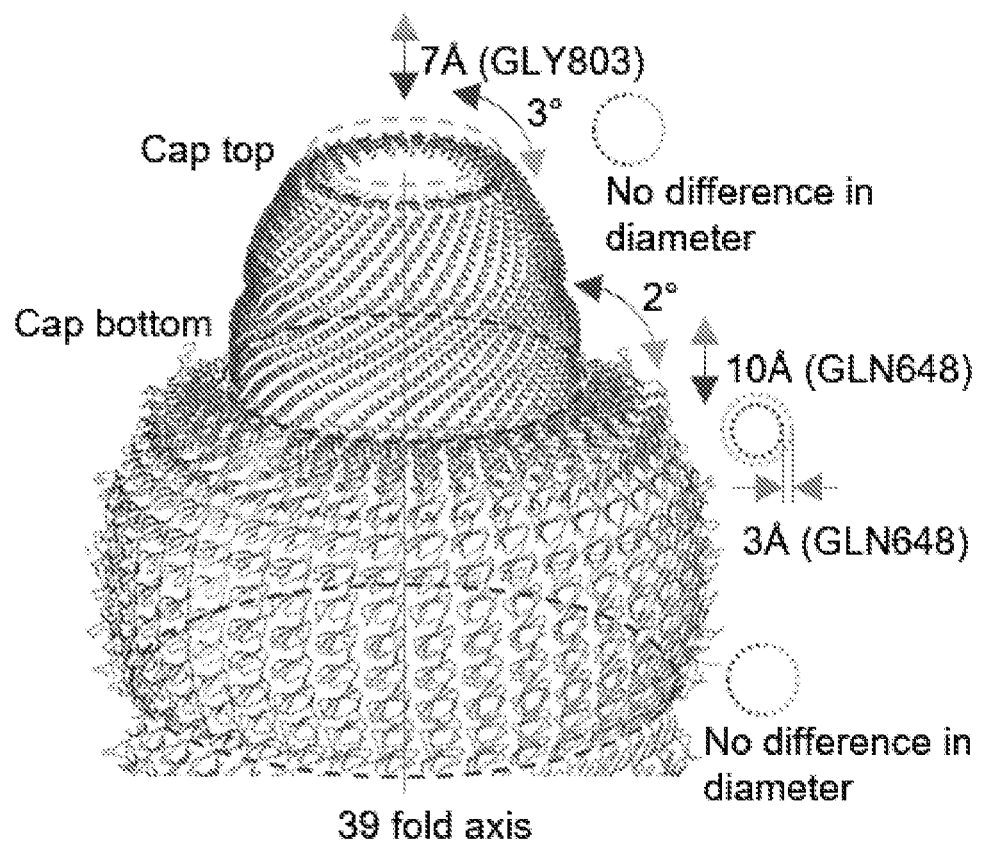
FIG. 11: A diagram to show the cap movement and conformational change between conformation 1 (purple) and conformation 2 (olive). In the refinement result applied D39 symmetry, the relative movement freedom of cap is limited to axial (up and down) and rotational (rotation around 39-fold axis). The movement from conformation 1 to conformation 2 of cap region can be described as "being rotated clockwise by 2 degrees and lifted by 10 Å". There is minor morphing of cap between the two conformations, when conformation 2 is relatively shorter and more twisted at cap region based on shorter translocation distance along axis and more angular rotation at cap-ring region.

Because of the linear arrangement of domains from N- to C-terminus, the large conformational change at the shoulder domain introduces a large translocation of the cap-helix and cap-ring domains (FIG. 7). In both conformations, α-helix and β-strands are resolved in the shoulder and cap-helix domains, allowing detailed comparisons of these high-resolution features to be compared in the two conformations (FIG. 7, Panels A and B). When viewed along the symmetry axis, the cap of conformation 2 is lifted by 10 Å and rotated by 2° clockwise from the bottom (FIG. 11, measurement based on $C_\alpha$ of GLN648) as compared to conformation 1. Further alignment shows that the cap top of conformation 2 was further rotated by 1° and shortened along the 39-fold axis by about 3 Å (measurement based on $C_\alpha$ of GLY803). The diameter of the cap top (i.e., the distance from $C_\alpha$ of GLY803 the symmetry axis) is the same in both conformations, while the cap bottom diameter of conformation 2 is 6 Å (i.e., 3%) larger than that of conformation 1. The 4.7 Å resolution of the cryoEM density further supports these model-based measurements.

Position and Structure of the Engineered HIV-1 Gag 148-214 Peptide Inside the Vault Weak densities are observed in both conformations at the waist region close to the N-terminus of MVP. These weak densities are interpreted to be the covalently attached HIV-1 Gag 148-214 peptide because of its connection to the N-terminus of MVP and its size matching that expected for the engineered Gag segment (FIG. 12, Panels A and B). The density of the covalently attached peptide is weaker than that of MVP (FIG. 12, Panels C and D) and the boundary of covalently attached protein at the waist region is at lower resolution. A dimer of Gag 148-214 (PDB 1AFV) (Momany et al., 1996) can be docked into the donut shaped density seen inside the waist region. However, the docking was not unique, and no secondary structure could be identified in the waist-ring density, suggesting that the fusion peptide is flexible inside the vault with only limited interactions with MVP. This result is consistent with previous observations that peptides covalently attached to N-terminus of MVP tend to extend towards the center of a vault particle (Mikyas et al., 2004).

The total number of amino acids for the covalently attached Gag 148-214 and the GFLGL (SEQ ID NO: 6) linker is 73. Applying the free chain model assuming a persistence length of 5 amino acids, the engineered peptide would give rise to a maximal end-to-end length of 73 Å (i.e., 3.8 Å×5×√(73/5)). This maximal length of the engineered segment is much shorter than the 140 Å axial linear distance between the R8 domain and the waist. Therefore, the observed conformational change starting at the R8 domain is unlikely caused by interactions with the covalently attached Gag 148-214 peptide.

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., J. Mol. Biol. 215:403-410 (1990). Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences. Alternatively, the comparison window can exist over the full length of the sequences being compared.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BEST-FIT, FASTA, and TFASTA in the Wisconsin Genetics Software Package, Genetics Computer Group, 575 Science Dr., Madison, Wis.), or by visual inspection.

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus.

Modified MVP R8 proteins of the present invention may be made using methods known in the art including chemical synthesis, biosynthesis or in vitro synthesis using recombinant DNA methods, and solid phase synthesis. See e.g., Kelly & Winkler (1990) Genetic Engineering Principles and Methods, vol. 12, J. K. Setlow ed., Plenum Press, N.Y., pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. Modified MVP R8 proteins of the present invention may be purified using protein purification techniques known in the art such as reverse phase high-performance liquid chromatography (HPLC), ion-exchange or immunoaffinity chromatography, filtration or size exclusion, or electrophoresis. See Olsnes and Pihl (1973) Biochem. 12 (16):3121-3126; and Scopes (1982) Protein Purification, Springer-Verlag, NY, which are herein incorporated by reference. Alternatively, polypeptides of the present invention may be made by recombinant DNA techniques known in the art. Thus, polynucleotides that encode the modified MVP R8 proteins of the present invention are contemplated herein. In some embodiments, the polypeptides and polynucleotides of the present invention are isolated.

As used herein, an "isolated" compound refers to a compound that is isolated from its native environment. For example, an isolated polynucleotide is a one which does not have the bases normally flanking the 5' end and/or the 3' end of the polynucleotide as it is found in nature. As another example, an isolated polypeptide is a one which does not have its native amino acids, which correspond to the full-length polypeptide, flanking the N-terminus, C-terminus, or both. For example, an isolated fragment of modified MVP R8 protein refers to an isolated polypeptide that consists of only a portion of the fusion MVP R8 protein or comprises some, but not all, of the amino acid residues fusion MVP R8 protein and non-native amino acids, i.e., amino acids that are different from the amino acids found at the corresponding positions of fusion MVP R8 protein, at its N-terminus, C-terminus, or both. In some embodiments, isolated polynucleotides and polypeptides of the present invention are made "by the hand of man", e.g., using synthetic and/or recombinant techniques.

In some embodiments, the modified R8 vaults and modified MVP R8 proteins of the present invention are substantially purified. As used herein, a "substantially purified" compound refers to a compound that is removed from its natural environment and/or is at least about 60% free, preferably about 75% free, and more preferably about 90% free, and most preferably about 95-100% free from other macromolecular components or compounds with which the compound is associated with in nature or from its synthesis.

Compositions of the present invention, including pharmaceutical compositions and vaccines, include one or more modified R8 vaults and/or one or more modified MVP R8 proteins.

The term "pharmaceutical composition" refers to a composition suitable for pharmaceutical use in a subject. A pharmaceutical composition generally comprises an effective amount of an active agent, e.g., one or more modified R8 vaults and/or one or more modified MVP R8 proteins, and a pharmaceutically acceptable carrier. The term "effective amount" refers to a dosage or amount sufficient to produce a desired result. The desired result may comprise an objective or subjective improvement in the recipient of the dosage or amount, e.g., long-term survival, effective prevention of a disease state, and the like. Pharmaceutical compositions according to the present invention may further include one or more active ingredients in addition to the one or more modified R8 vaults and/or one or more modified MVP R8 proteins.

One or more modified R8 vaults and/or one or more modified MVP R8 proteins may be administered, preferably in the form of pharmaceutical compositions, to a subject. Preferably the subject is mammalian, more preferably, the subject is human. Preferred pharmaceutical compositions are those comprising at least one modified R8 vault and/or at least one modified MVP R8 protein in a therapeutically effective amount or an immunogenic amount, and a pharmaceutically acceptable vehicle.

Vaccines according to the present invention provide a protective immune response when administered to a subject. As used herein, a "vaccine" according to the present invention is a pharmaceutical composition that comprises an immunogenic amount of at least one modified R8 vault and/or at least one modified MVP R8 protein and provides a protective immune response when administered to a subject. The protective immune response may be complete or partial, e.g., a reduction in symptoms as compared with an unvaccinated subject.

As used herein, an "immunogenic amount" is an amount that is sufficient to elicit an immune response in a subject and depends on a variety of factors such as the immunogenicity of the given immunogen, the degree of the given disease or condition to be treated, the manner of administration, the general state of health of the subject, and the like. The typical immunogenic amounts for initial and boosting immunizations for therapeutic or prophylactic administration may range from about 120 μg to 8 mg per kilogram of body weight of a subject. For example, the typical immunogenic amount for initial and boosting immunization for therapeutic or prophylactic administration for a human subject of 70 kg body weight ranges from about 8.4 mg to about 560 mg, preferably about 10-100 mg, more preferably about 10-20 mg, per about 65-70 kg body weight of a subject. Examples of suitable immunization protocols include an initial immunization injection (time 0), followed by booster injections at 4, and/or 8 weeks, which these initial immunization injections may be followed by further booster injections at 1 or 2 years if needed.

As used herein, a "therapeutically effective amount" refers to an amount that may be used to treat, prevent, or inhibit a given disease or condition, in a subject as compared to a control. Again, the skilled artisan will appreciate that certain factors may influence the amount required to effectively treat a subject, including the degree of the given disease or condition to be treated, previous treatments, the general health and age of the subject, and the like. Nevertheless, therapeutically effective amounts may be readily determined by methods in the art. It should be noted that treatment of a subject with a therapeutically effective amount or an immunogenic amount may be administered as a single dose or as a series of several doses. The dosages used for treatment may increase or decrease over the course of a given treatment. Optimal dosages for a given set of conditions may be ascertained by those skilled in the art using dosage-determination tests and/or diagnostic assays in the art. Dosage-determination tests and/or diagnostic assays may be used to monitor and adjust dosages during the course of treatment.

The compositions of the present invention may include an adjuvant. As used herein, an "adjuvant" refers to any substance which, when administered in conjunction with (e.g., before, during, or after) a pharmaceutically active agent, such as a modified R8 vault according to the present invention, aids the pharmaceutically active agent in its mechanism of action. Thus, an adjuvant in a vaccine according to the present invention is a substance that aids the at least one modified R8 vault in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by methods in the art. In some embodiments, the modified R8 vaults act as an adjuvant. In some embodiments, the modified R8 vaults contain an adjuvant as passively packaged passenger molecule.

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions, or emulsions, as well as sterile powders for reconstitution into sterile injectable solutions or dispersions. The compositions and formulations of the present invention may be optimized for increased stability and efficacy using methods in the art. See, e.g., Carra et al. (2007) Vaccine 25:4149-4158, which is herein incorporated by reference.

The compositions of the present invention may be administered to a subject by any suitable route including oral, transdermal, subcutaneous, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular modified R8 vault and/or modified MVP R8 protein used.

As used herein, a "pharmaceutically acceptable vehicle" or "pharmaceutically acceptable carrier" are used interchangeably and refer to solvents, dispersion media, coatings, antibacterial and antifungal agents, isotonic and absorption delaying agents, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. As used herein, a "dosage unit form" refers to physically discrete units suited as unitary dosages for the subject to be treated; each unit containing a predetermined quantity of the one or more modified R8 vaults and/or the one or more modified MVP R8 proteins calculated to produce the desired therapeutic effect in association with the required pharmaceutically acceptable carrier. The specification for the dosage unit forms of the invention are dictated by and directly dependent on the unique characteristics of the given modified R8 vault and/or the given modified MVP R8 protein and desired therapeutic effect to be achieved, and the limitations inherent in the art of compounding such an active compound for the treatment of individuals.

In some embodiments, the present invention provides a method of making a pharmaceutical composition, which comprises combining one or more modified R8 vaults as described herein and/or one or more modified MVP R8 proteins as described herein with a pharmaceutically acceptable carrier. In some embodiments, the method further comprises using recombinant DNA techniques and/or protein engineering methods in the art to produce the one or more modified MVP R8 proteins. In some embodiments, the method further comprises using recombinant DNA techniques to insert a passenger molecule such as a passenger peptide into the R8 flexible region of an MVP protein. In some embodiments, the MVP protein has about 90-100%, more preferably about 95-100%, and most preferably 97-100% sequence identity to human MVP. In some embodiments, the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4. In some embodiments, the MVP protein has about 90-100%, more preferably about 95-100%, and most preferably 97-100% sequence identity to human MVP and the R8 flexible region comprises about 15 to 32 amino acid residues of a sequence that has about at least about 70%, preferably about 75-100%, more preferably about 80-100%, even more preferably about 85-100%, and most preferably about 90-100% sequence identity to SEQ ID NO: 4.

Toxicity and therapeutic efficacy of modified R8 vaults and modified MVP R8 proteins according to the instant invention and compositions thereof can be determined using cell cultures and/or experimental animals and pharmaceutical procedures in the art. For example, one may determine the lethal dose, $LC_{50}$ (the dose expressed as concentration× exposure time that is lethal to 50% of the population) or the $LD_{50}$ (the dose lethal to 50% of the population), and the $ED_{50}$ (the dose therapeutically effective in 50% of the population) by methods in the art. The dose ratio between toxic and therapeutic effects is the therapeutic index and it can be expressed as the ratio $LD_{50}/ED_{50}$. Modified R8 vaults and modified MVP R8 proteins which exhibit large therapeutic indices are preferred. While modified R8 vaults and modified MVP R8 proteins that result in toxic side-effects may be used, care should be taken to design a delivery system that targets such compounds to the site of treatment to minimize potential damage to uninfected cells and, thereby, reduce side-effects.

The data obtained from the cell culture assays and animal studies can be used in formulating a range of dosages for use in humans. Preferred dosages provide a range of circulating concentrations that include the $ED_{50}$ with little or no toxicity. The dosage may vary depending upon the dosage form employed and the route of administration utilized. Therapeutically effective amounts and dosages of modified R8 vaults and modified MVP R8 proteins according to the present invention can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additionally, a dosage suitable for a given subject can be determined by an attending physician or qualified medical practitioner, based on various clinical factors.

In some embodiments, the present invention is directed to kits which comprise one or more modified R8 vaults and/or one or more modified MVP R8 proteins, optionally in the form of a composition, packaged together with one or more reagents, containers, or drug delivery devices. Such kits include a carrier, package, or container that may be compartmentalized to receive one or more containers, such as vials, tubes, and the like. In some embodiments, the kits optionally include an identifying description or label or instructions relating to its use. In some embodiments, the kits comprise the one or more modified R8 vaults and/or the one or more modified MVP R8 proteins, optionally in one or more unit dosage forms, packaged together as a pack and/or in drug delivery device, e.g., a pre-filled syringe. In some embodiments, the kits include information prescribed by a governmental agency that regulates the manufacture, use, or sale of compounds and compositions according to the present invention.

The following examples are intended to illustrate but not to limit the invention.

EXAMPLES

Recombinant Vault Sample Preparation

The HIV Gag 148-214-GFLGL fragment was PCR amplified and cloned into pFastBac 1 containing rat MVP. The NcoI cloning site at the MVP 5' end was used as a site of insertion by employing In-Fusion HD cloning kit (cat #638910) and by strictly following the In-Fusion® HD Cloning kit manual from Takara/Clontech Inc. The resulting pFastBac1 construct was recombined with Bacmid DNA in MAX Efficiency® DH10Bac™ Competent Cells from Invitrogen (cat #10361012), see manufacturers protocol. The Bacmid containing the Gag 148-214-GFLGL-MVP recombinant DNA was purified following Bac-to-Bac® Baculovirus Expression System manual from Invitrogen (cat #10359-016). Generation of Baculovirus expressing the recombinant MVP was accomplished by transfecting Gibco® Sf-900™ II SFM cells (cat #11496015) with Bacmid containing DNA. Follow the Gibco® Sf-900™ II SFM manufacturer's protocol. To produce the recombinant vaults, $1 \times 10^8$ cells (Gibco® Sf-900™ II SFM) were infected with the recombinant Baculovirus in 50 ml Sf-900™ II SFM (cat #10902096). The infected cells were shaken for 3 to 4 days at 28° C., then harvested by centrifuging at 500×g for 5 minutes at room temperature. Cell pellet was stored at −80° C. or used directly for vault purification.

For Sf9 cell lysis, buffer A (50 mM Tris-Cl buffer, 75 mM NaCl, 0.5 mM MgCl2) containing 2% Triton-X-100, 2% PI (Protease Inhibitor; Sigma-Aldrich P8849-5ML) and 1 mM PMSF (Phenylmethylsulfonyl fluoride) was prepared. 1 mg of RNase A was added to 1 g of Sf9 cells expressing Gagl-M1-GFLGL-rMVP, then 5 ml of lysis buffer was added and incubated on ice for 15 minutes. 2 mM DTT was then added and the cell lysate was further incubated on ice for additional 5 minutes. The lysate was centrifuged at 20,000×g at 4° C. for 20 minutes. The supernatant was collected and centrifuged at 40K in Ti 70.1 rotor for 1 hour at 4° C. The pellet was resuspended in 1 ml buffer A supplemented with 2% PI, 2 mM PMSF, and 2 mM DTT. 1 ml Ficoll-sucrose was added and the mixture was further vortexed and centrifuged at 25K in Ti 70.1 rotor at 4° C. for 10 minutes. The supernatant was diluted with 5.5 ml buffer A supplemented with 1% PI, 1 mM PMSF and 1 mM DTT, which was then centrifuged at 40 K in Ti 70.1 rotor for 1 h, 30 minutes at 4° C. The pellet was resuspended in 1 ml buffer A containing 1% PI, 1 mM PMSF and 1 mM DTT. 5 µg streptomycin sulfate was added; the mixture was tumbled at room temperature for 30 minutes, then centrifuged 16,100×g at room temperature for 10 minutes. Clarified supernatant was overlaid on a stepwise sucrose gradient (20%, 30%, 40%, 45%, 50%, 60% sucrose, 1.5 ml each) and then centrifuged at 25K in sw41 rotor at 4° C. for 16 hours. The 40% and 45% sucrose fractions were collected. The fractions were diluted in 4.5 ml PBS, then centrifuged at 40K in Ti 70.1 rotor at 4° C. for 2 hours. The pellet was resuspended in 210 µl PBS to serve as cryoEM grid ready sample.

Electron Microscopy and Movie Processing

For cryoEM, an aliquot of 2.5 µl of recombinant vault sample was applied to each EM grid with Lacey carbon films. The grid was blotted with Vitrobot in 100% humidity for 10 s and then plunged into liquid ethane to vitrify the sample. Movies were obtained in Titan Krios 300 kV electron microscope with Gatan K2 direct election detection camera in super-resolution mode with Leginon (Mindell and Grigorieff, 2003) at ×49000. The pixel size was measured to be 1.036 Å on the specimen scale. An electron dose rate of 8 electrons/pixel/second was used and each movie contains 20 frames recorded in 5 seconds. Image stacks in each movie were aligned with UCSF MotionCorr (Li et al., 2013). The first 16 frames in each stack were averaged to obtain an image sum of 32 e$^-$/Å$^2$. the whole dataset has 1218 movies.

Data Processing and 3D Reconstruction

Figure 14:
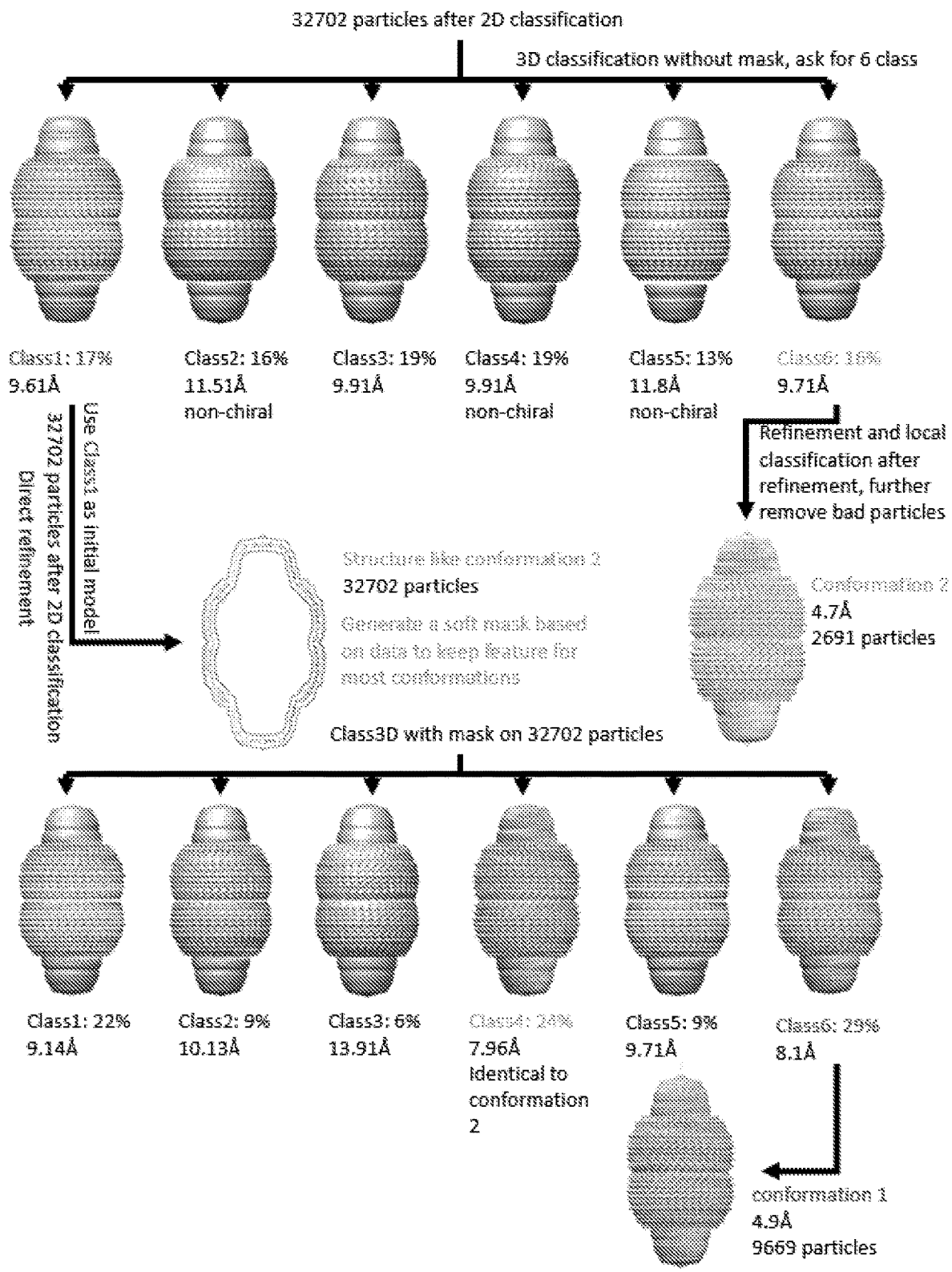
FIG. 14: Classification and refinement process. Multiple conformations was found in initial classification. Further classification with soft mask was later conducted to increase classification accuracy. Structure chirality and cap-helix quality are major features to distinguish a good 3D class.

Micrographs after alignment were used for contrast transfer function (CTF) determination in CTFFIND3 (Mindell and Grigorieff, 2003), with defocus values ranging from −1.7 µm to −4.2 µm. A total of 63751 particles were manually picked with 900×900 box size in pixel. Particles were first directly refined with Frealign (Lyumkis et al., 2013) and reported resolution was 13.5 Å with little features showing handedness. Then, all particles were subjected RELION 1.2 (Scheres, 2012) for two-dimensional classifications (Class2D). Top views were intentionally excluded from further classification to limit sampling space and to accelerate refinement process. Also, classes with no interpretable features were discarded. 32702 particles were selected for further three-dimensional classifications (Class3D). Particles are classified based on D38, D39 and D40 symmetry in different runs. Classification result with D38 and D40 symmetry also showed little feature with handedness. The following class3D are all conducted applying D39 symmetry with finer searching grid (FIG. 14). The initial model for Class3D was generated from previously published atomic model (PDB 4HL8) of rat vault to 50 Å resolution to eliminate the potential risk of model bias. Class3D analysis was conducted with D39 fold symmetry applied and 2 distinguish classes with relatively good resolution (about 9 Å) were found. These two classes were further refined separately with RELION 1.2 with D39 symmetry. To further enhance signal, mask is generated from cryoEM data to focus the refinement on MVP region. Following the "gold standard" refinement protocol described by Scheres, the two conformations were refined both to near-atomic resolution after RELION post-processing and automatic soft masking (Scheres, 2012). The resolution was determined based on a "gold standard" Fourier shell correlation (FSC) coefficient of 0.143 according to Scheres (Scheres, 2012).

Atomic Model Building, Refinement, and Visualization

The atomic model of engineered vault was derived from crystal structure PDB 4HL8. By calibrating pixel size from 1.036 Å to 1.000 Å, an optimal docking of PDB 4HL8 into conformation 1 density was achieved. The fitted PDB 4HL8 was subjected to real-space refinement in Phenix (Adams et al., 2010) using the MVP monomer as density map input. Ramachandran and rotamer outliers were manually corrected with Coot (Emsley et al., 2010) for this conformation 1 model.

The pixel size of conformation 2 density was also adjusted to 1.000 Å accordingly. R1-R7 domains in PDB 4HL8 was first fitted into conformation 2 density. In R8 to cap-helix domains of PDB 4HL8, individual secondary structures were fitted into corresponding densities in conformation 2 map. Those secondary structures were further connected with linker accordingly to create a "morphed" model. Following the same protocol as the refining model of conformation 1, this "morphed" PDB 4HL8 was subjected to real-space refinement with segmented density of conformation 2 in Phenix. Ramachandran and rotamer outliers were also manually corrected with Coot (Emsley et al., 2010) for conformation 2.

Visualization and map segment were achieved with UCSF Chimera (Pettersen et al., 2004). Local resolution was calculated by Resmap (Kucukelbir et al., 2014).

R8 Flexible Region Modification and Packaging

An AfeI cloning site was introduced into the nucleotide sequence encoding human MVP (SEQ ID NO: 7) by PCR amplification of pFastBac1-hMVP sequence using the following primers:

```
Forward:
                                    (SEQ ID NO: 8)
GCTGAGAAGGACACAGCTAAGAGCCT Reverse:
                                    (SEQ ID NO: 9)
GCTACCCCTGTCTGCCAGAGGGTCCT
```

The resulting PCR product was agarose gel purified and subsequently circularized by KLD Enzyme Mix (NEB, Cat. #M0554S), accordingly to the manufacturers protocol. The sequence of the clone was analyzed to confirm the correct AfeI insertion into pFastBac1-hMVP construct.

The HIV sequences inserted into the AfeI site and the encoded HIV peptides were:

```
Gag1-M1:
                                    (SEQ ID NO: 10)
ATGACCCCCCGGACCCTGAACGCCTGGGTCAAGGTGGTGGAAGAGAAGGCC

TTCAGCCCCGAAGTGATCCCCATGTTCACCGCCCTGAGCGAGGGCGCCACC

CCCAGCGACCTGAACACCATGCTGAATACCATCGGCGGCCACCAGGCCGCC

ATGCAGATGCTGAAGGACACCATCAACGAAGAGGCCGCCGAGTGGGACCGG

Gag1-M1 (68 aa):
                                    (SEQ ID NO: 11)
MTPRTLNAWVKVVEEKAFSPEVIPMFTALSEGATPSDLNTMLNTIGGHQAA

MQMLKDTINEEAAEWDR

Gag2-M1:
                                    (SEQ ID NO: 12)
ATGAACCCCCCCATCCCCGTGGGCGACATCTACAAGCGGTGGATCATCCTG

GGCCTGGACAAGATCGTGCGGATGTACAGCCCCACCAGCATCCTGGACATC

CGGCAGGGCCCCAAAGAGCCCTTCCGGGACTACGTGGACCGGTTCTTCAAG

GTGCTGCGGGCCGAGCAGGCCACCCAGGACGTGAAGAACTGGATGACCGAC

ACCCTGCTGGTGCAGAACGCCAACCCCGACTGCAAGACCATCCTGAGAGCC

CTGGGC

Gag2-M1 (87 aa):
                                    (SEQ ID NO: 13)
MNPPIPVGDIYKRWIILGLDKIVRMYSPTSILDIRQGPKEPFRDYVDRFFK

VLRAEQATQDVKNWMTDTLLVQNANPDCKTILRALG

Env-M1:
                                    (SEQ ID NO: 14)
ATGGGCTTTCTGGGCGTGGCCGGCAGCACAATGGGAGCCGCCAGCATCACC

CTGACCGTGCAGGCCAGACAGCTGCTGAGCGGCATCGTGCAGCAGCAGAGC

AACCTGCTGAGAGCTATCGAGGCCCAGCAGCATCTGCTGAAGCTGACCGTG

TGGGGCATCAAGCAGCTGCAGACCCGGGTGCTGGCCATCGAGAGATACCTG

AAGGACCAGCAGCTCCTGGGCCTGTGGGGCTGCAGCGGCAAGCTGATCTGC

CCCACC

Env-M1 (87 aa):
                                    (SEQ ID NO: 15)
MGFLGVAGSTMGAASITLTVQARQLLSGIVQQQSNLLRAIEAQQHLLKLTV

WGIKQLQTRVLAIERYLKDQQLLGLWGCSGKLICPT

Nef-M1:
                                    (SEQ ID NO: 16)
ATGCGGCAGGAAATCCTGGACCTCTGGGTGTACCACACCCAGGGATTCTTC

CCAGACTGGCAGAACTACACCCCCGGACCCGGCATCAGATACCCCCTGACC

TTCGGCTGGTGCTACAAGCTGGTGCCCGTG

Nef-M1 (44 aa):
                                    (SEQ ID NO: 17)
MRQEILDLWVYHTQGFFPDWQNYTPGPGIRYPLTFGWCYKLVPV
```

The primers used to insert the HIV sequences into the AfeI site were:

```
Gag1-M1
Forward:
                                    (SEQ ID NO: 18)
GGCAGACAGGGGTAGCATGACCCCCCGGACCCTGAACG Reverse:
                                    (SEQ ID NO: 19)
GCTGTGTCCTTCTCAGCCCGGTCCCACTCGGCGGCCT Gag2-M1
Forward:
                                    (SEQ ID NO: 20)
GGCAGACAGGGGTAGCATGAACCCCCCCATCCCCGT Reverse:
                                    (SEQ ID NO: 21)
GCTGTGTCCTTCTCAGCGCCCAGGGCTCTCAGGATGG Env-M1
Forward:
                                    (SEQ ID NO: 22)
GGCAGACAGGGGTAGCATGGGCTTTCTGGGCGTGGC Reverse:
                                    (SEQ ID NO: 23)
GCTGTGTCCTTCTCAGCGGTGGGGCAGATCAGCTTG Nef-M1
Forward:
                                    (SEQ ID NO: 24)
GGCAGACAGGGGTAGCATGCGGCAGGAAATCCTGGA
```

Reverse:
(SEQ ID NO: 25)
GCTGTGTCCTTCTCAGCCACGGGCACCAGCTTGTAG

The mCherry sequence inserted into the AfeI site and the encoded peptide were:

mCherry:
(SEQ ID NO: 26)
ATGGTGAGCAAGGGCGAGGAGGATAACATGGCCATCATCAAGGAGTTCATG

CGCTTCAAGGTGCACATGGAGGGCTCCGTGAACGGCCACGAGTTCGAGATC

GAGGGCGAGGGCGAGGGCCGCCCCTACGAGGGCACCCAGACCGCCAAGCTG

AAGGTGACCAAGGGTGGCCCCCTGCCCTTCGCCTGGGACATCCTGTCCCCT

CAGTTCATGTACGGCTCCAAGGCCTACGTGAAGCACCCCGCCGACATCCCC

GACTACTTGAAGCTGTCCTTCCCCGAGGGCTTCAAGTGGGAGCGCGTGATG

AACTTCGAGGACGGCGGCGTGGTGACCGTGACCCAGGACTCCTCCCTGCAG

GACGGCGAGTTCATCTACAAGGTGAAGCTGCGCGGCACCAACTTCCCCTCC

GACGGCCCCGTAATGCAGAAGAAGACCATGGGCTGGGAGGCCTCCTCCGAG

CGGATGTACCCCGAGGACGGCGCCCTGAAGGGCGAGATCAAGCAGAGGCTG

AAGCTGAAGGACGGCGGCCACTACGACGCTGAGGTCAAGACCACCTACAAG

GCCAAGAAGCCCGTGCAGCTGCCCGGCGCCTACAACGTCAACATCAAGTTG

GACATCACCTCCCACAACGAGGACTACACCATCGTGGAACAGTACGAACGC

GCCGAGGGCCGCCACTCCACCGGCGGCATGGACGAGCTGTACAAG mCherry (236 aa):
(SEQ ID NO: 27)
MVSKGEEDNMAIIKEFMRFKVHMEGSVNGHEFEIEGEGEGRPYEGTQTAKL

KVTKGGPLPFAWDILSPQFMYGSKAYVKHPADIPDYLKLSFPEGFKWERVM

NFEDGGVVTVTQDSSLQDGEFIYKVKLRGTNFPSDGPVMQKKTMGWEASSE

RMYPEDGALKGEIKQRLKLKDGGHYDAEVKTTYKAKKPVQLPGAYNVNIKL

DITSHNEDYTIVEQYERAEGRHSTGGMDELYK

The primers used to insert mCherry into the AfeI site were:

Forward:
(SEQ ID NO: 28)
GGCAGACAGGGGTAGCATGGTGAGCAAGGGCGAGGAGGAT

Reverse:
(SEQ ID NO: 29)
GCTGTGTCCTTCTCAGCCTTGTACAGCTCGTCCATG

Cloning into the AfeI site within the R8 flexible region was achieved by In-Fusion HD cloning kit (cat #638910) and by strictly following the In-Fusion® HD Cloning kit manual from Takara/Clontech Inc.

The following set of primers were used to replace the entire R8 flexible region with only the AfeI site:

Forward:
(SEQ ID NO: 30)
GCTTTGGCGCCCCGGAACAAGACCCGT

Reverse:
(SEQ ID NO: 31)
GCTGTTCAGCAGCTCCTCCACCCCGGGA

Vault particles made from the nucleic acid molecules encoding the modified MVP R8 proteins (human MVP having a passenger peptides in the AfeI site in the R8 flexible region, human MVP having an AfeI site in the R8 flexible region and no passenger peptide, and human MVP having an AfeI site in place of the R8 flexible region (i.e., Ser-Ala in place of the entire R8 flexible region) made using cell-free techniques in the art and the structures of the vault particles were examined. The vault particles exhibited barrel-like structures that are the same or substantially similar vault particles made using unmodified human MVP. These experiments evidence that modified R8 vaults according to the present invention can contain only 2 amino acids in place of its R8 flexible region and can include a passenger peptide of up to 236 amino acids.

REFERENCES

The following references are herein incorporated by reference in their entirety.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D 66, 213-221.

Anderson, D. H., Kickhoefer, V. A., Sievers, S. A., Rome, L. H., and Eisenberg, D. (2007). Draft crystal structure of the vault shell at 9-angstrom resolution. Plos Biol 5, 2661-2670.

Berger, W., Steiner, E., Grusch, M., Elbling, L., and Mickshe, M. (2009). Vaults and the major vault protein: Novel roles in signal pathway regulation and immunity. Cell Mol Life Sci 66, 43-61.

Buehler, D. C., Toso, D. B., Kickhoefer, V. A., Zhou, Z. H., and Rome, L. H. (2011). Vaults Engineered for Hydrophobic Drug Delivery. Small 7, 1432-1439.

Casanas, A., Querol-Audi, J., Guerra, P., Pous, J., Tanaka, H., Tsukihara, T., Verdaguer, N., and Fita, I. (2013). New features of vault architecture and dynamics revealed by novel refinement using the deformable elastic network approach. Acta Crystallogr D 69, 1054-1061.

Champion, C. I., Kickhoefer, V. A., Liu, G. C., Moniz, R. J., Freed, A. S., Bergmann, L. L., Vaccari, D., Raval-Fernandes, S., Chan, A. M., Rome, L. H., et al. (2009). A Vault Nanoparticle Vaccine Induces Protective Mucosal Immunity. Plos One 4.

Emsley, P., Lohkamp, B., Scott, W. G., and Cowtan, K. (2010). Features and development of Coot. Acta Crystallogr D 66, 486-501.

Kedersha, N. L., Miguel, M. C., Bittner, D., and Rome, L. H. (1990). Vaults .2. Ribonucleoprotein Structures Are Highly Conserved among Higher and Lower Eukaryotes. J Cell Biol 110, 895-901.

Kedersha, N. L., and Rome, L. H. (1986). Isolation and characterization of a novel ribonucleoprotein particle: large structures contain a single species of small RNA. J. Cell Biol. 103, 699-709.

Kickhoefer, V. A., Han, M., Raval-Fernandes, S., Poderycki, M. J., Moniz, R. J., Vaccari, D., Silvestry, M., Stewart, P. L., Kelly, K. A., and Rome, L. H. (2009). Targeting Vault Nanoparticles to Specific Cell Surface Receptors. Acs Nano 3, 27-36.

Kong, L. B., Siva, A. C., Rome, L. H., and Stewart, P. L. (1999). Structure of the vault, a ubiquitous cellular component. Struct Fold Des 7, 371-379.

Kucukelbir, A., Sigworth, F. J., and Tagare, H. D. (2014). Quantifying the local resolution of cryo-EMEM density maps. Nat Methods 11, 63-+.

Li, X. M., Mooney, P., Zheng, S., Booth, C. R., Braunfeld, M. B., Gubbens, S., Agard, D. A., and Cheng, Y. F. (2013). Electron counting and beam-induced motion correction enable near-atomic-resolution single-particle cryo-EM. Nat Methods 10, 584-+.

Lyumkis, D., Brilot, A. F., Theobald, D. L., and Grigorieff, N. (2013). Likelihood-based classification of cryo-EM images using FREALIGN. J Struct Biol 183, 377-388.

Mikyas, Y., Makabi, M., Raval-Fernandes, S., Harrington, L., Kickhoefer, V. A., Rome, L. H., and Stewart, P. L. (2004). Cryoelectron microscopy imaging of recombinant and tissue derived vaults: Localization of the MVP N termini and VPARP. J Mol Biol 344, 91-105.

Mindell, J. A., and Grigorieff, N. (2003). Accurate determination of local defocus and specimen tilt in electron microscopy. J Struct Biol 142, 334-347.

Momany, C., Kovari, L. C., Prongay, A. J., Keller, W., Gitti, R. K., Lee, B. M., Gorbalenya, A. E., Tong, L., McClure, J., Ehrlich, L. S., et al. (1996). Crystal structure of dimeric HIV-1 capsid protein. Nat Struct Biol 3, 763-770.

Mrazek, J., Toso, D., Ryzantsev, S., Zhang, X., Zhou, Z. H., Fernandez, B. C., Kickhoefer, V. A., and Rome, L. H. (2014). Polyribosomes Are Molecular 3D Nanoprinters That Orchestrate the Assembly of Vault Particles. Acs Nano 8, 11552-11559.

Pettersen, E. F., Goddard, T. D., Huang, C. C., Couch, G. S., Greenblatt, D. M., Meng, E. C., and Ferrin, T. E. (2004). UCSF chimera—A visualization system for exploratory research and analysis. J Comput Chem 25, 1605-1612.

Poderycki, M. J., Kickhoefer, V. A., Kaddis, C. S., Raval-Fernandes, S., Johansson, E., Zink, J. I., Loo, J. A., and Rome, L. H. (2006). The vault exterior shell is a dynamic structure that allows incorporation of vault-associated proteins into its interior. Biochemistry-Us 45, 12184-12193.

Qi, X. Y., Huang, X., Li, H., Wang, Y. S., Xia, Y., Natarajan, M., Wei, J., Venkatraman, S. S., and Zhang, H. (2012). Vault Protein-Templated Assemblies of Nanoparticles. Nano 7.

Querol-Audi, J., Casanas, A., Uson, I., Luque, D., Caston, J. R., Fita, I., and Verdaguer, N. (2009). The mechanism of vault opening from the high resolution structure of the N-terminal repeats of MVP. Embo J 28, 3450-3457.

Scheres, S. H. W. (2012). RELION: Implementation of a Bayesian approach to cryo-EM structure determination. J Struct Biol 180, 519-530.

Shaner N C, Campbell R E, Steinbach P A, Giepmans B N, Palmer A E, Tsien R Y. (2006). Improved Monomeric Red, Orange and Yellow Fluorescent Proteins Derived from Discosoma Sp. Red Fluorescent Protein. Nat Biotechnol. 22, 1567-1572.

Slesina, M., Inman, E. M., Moore, A. E., Goldhaber, J. I., Rome, L. H., and Volknandt, W. (2006). Movement of vault particles visualized by GFP-tagged major vault protein. Cell Tissue Res 324, 403-410.

Stephen, A. G., Raval-Fernandes, S., Huynh, T., Torres, M., Kickhoefer, V. A., and Rome, L. H. (2001). Assembly of vault-like particles in insect cells expressing only the major vault protein. J Biol Chem 276, 23217-23220.

Tanaka, H., Kato, K., Yamashita, E., Sumizawa, T., Zhou, Y., Yao, M., Iwasaki, K., Yoshimura, M., and Tsukihara, T. (2009). The Structure of Rat Liver Vault at 3.5 Angstrom Resolution. Science 323, 384-388.

Tanaka, H., and Tsukihara, T. (2012). Structural studies of large nucleoprotein particles, vaults. P Jpn Acad B-Phys 88, 416-433.

Yang, O. O., Ali, A., Kasahara, N., Faure-Kumar, E., Bae, J. Y., Picker, L. J., and Park, H. (2015). Short Conserved Sequences of HIV-1 Are Highly Immunogenic and Shift Immunodominance. J Virol 89, 1195-1204.

All scientific and technical terms used in this application have meanings commonly used in the art unless otherwise specified.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises or consists of" is used as a tool to avoid excess page and translation fees and means that in some embodiments the given thing at issue comprises something, and in some embodiments the given thing at issue consists of something. For example, the sentence "In some embodiments, the composition comprises or consists of A" is to be interpreted as if written as the following two separate sentences: "In some embodiments, the composition comprises A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A protein that comprises about 95-100% sequence identity to human MVP (Accession No. AAH15623.1) or rat MVP (Accession No. NP_073206.2), wherein the region of the protein that corresponds to amino acid position 428 to amino acid position 449 of human MVP (the "R8 flexible region") consists of 2-5, 5-10, or 10-15 amino acid residues.

2. A protein that comprises about 95-100% sequence identity to human MVP (Accession No. AAH15623.1) or rat MVP (Accession No. NP 073206.2), wherein the region of the protein that corresponds to amino acid position 428 to amino acid position 449 of human MVP (the "R8 flexible region") comprises a passenger molecule, wherein said passenger molecule is a peptide that is heterologous to the protein.

3. The protein according to claim 1, and further comprising a passenger molecule linked to the N-terminal end of the protein and/or a passenger molecule linked to the C-terminal end of the protein.

4. A vault particle comprising a protein according to claim 1.

5. A vault particle comprising a protein according to claim 1, and further comprising a passenger molecule linked to the N-terminal end of the protein and/or a passenger molecule linked to the C-terminal end of the protein.

6. The vault particle according to claim 4, and further comprising a passively packaged passenger molecule and/or an mINT passenger molecule.

7. A composition comprising one or more proteins according to claim 1.

8. The composition according to claim 7, and further comprising an adjuvant.

9. The composition according to claim 7, and further comprising a pharmaceutically acceptable carrier.

10. A method of administering a passenger molecule to a subject which comprises administering to the subject a protein according to claim 3; a vault particle comprising the protein; and/or a composition comprising the protein or the vault particle comprising the protein.

11. The method according to claim 10, wherein an immunogenic amount of the passenger molecule, the protein, and/or the vault particle is administered to the subject.

12. The protein according to claim 3, wherein the passenger molecule is a passenger peptide.

13. The vault particle according to claim 5, and further comprising a passively packaged passenger molecule and/or an mINT passenger molecule.

14. The protein according to claim 2, and further comprising a passenger molecule linked to the N-terminal end of the protein and/or a passenger molecule linked to the C-terminal end of the protein.

15. A vault particle comprising a protein according to claim 2.

16. A vault particle comprising a protein according to claim 2, and further comprising a passenger molecule linked to the N-terminal end of the protein and/or a passenger molecule linked to the C-terminal end of the protein.

17. The vault particle according to claim 15, and further comprising a passively packaged passenger molecule and/or an mINT passenger molecule.

18. A composition comprising one or more proteins according to claim 2.

19. The composition according to claim 18, and further comprising an adjuvant.

20. The composition according to claim 18, and further comprising a pharmaceutically acceptable carrier.

21. A method of administering a passenger molecule to a subject which comprises administering to the subject a protein according to claim 2; a vault particle comprising the protein; and/or a composition comprising the protein or the vault particle comprising the protein.

22. The method according to claim 21, wherein an immunogenic amount of the passenger molecule, the protein, and/or the vault particle is administered to the subject.

23. The protein according to claim 2, wherein the passenger molecule is a passenger peptide.

24. The vault particle according to claim 16, and further comprising a passively packaged passenger molecule and/or an mINT passenger molecule.

* * * * *